United States Patent [19]

Angelucci et al.

[11] Patent Number: 5,776,458
[45] Date of Patent: Jul. 7, 1998

[54] ANTHRACYCLINE-CONJUGATES

[75] Inventors: Francesco Angelucci; Daniela Ruggieri; Stefania Stefanelli; Antonino Suarato; Laura Bersani, all of Milan, Italy

[73] Assignee: Pharmacia & Upjohn S.p.A., Milan, Italy

[21] Appl. No.: 412,220

[22] Filed: Mar. 27, 1995

Related U.S. Application Data

[63] Continuation of Ser. No. 917,064, filed as PCT/EP91/02284, Dec. 3, 1991, abandoned.

[30] Foreign Application Priority Data

Dec. 5, 1990 [GB] United Kingdom ............... 9026491

[51] Int. Cl.$^6$ .................. A61K 39/395; A61K 39/00; C07K 16/00; C07K 17/00
[52] U.S. Cl. ................. 424/178.1; 424/179.1; 424/184.1; 530/391.7; 530/391.9
[58] Field of Search ............... 530/391.7, 391.9; 424/181.1, 178.1, 179.1

[56] References Cited

U.S. PATENT DOCUMENTS

| | | |
|---|---|---|
| 4,671,958 | 6/1987 | Rodwell et al. |
| 4,672,057 | 6/1987 | Bargiotti |
| 4,950,738 | 8/1990 | King et al. ............... 530/322 |
| 5,017,693 | 5/1991 | Hylarides et al. ............... 530/391.1 |
| 5,045,451 | 9/1991 | Uhr et al. ............... 435/7.23 |
| 5,106,951 | 4/1992 | Morgan et al. ............... 530/391.9 |
| 5,122,368 | 6/1992 | Greenfield ............... 530/327 |

FOREIGN PATENT DOCUMENTS

| | | |
|---|---|---|
| 70117/91 | 1/1991 | Australia. |
| 0014853 | 9/1980 | European Pat. Off. |
| 0039060 | 11/1981 | European Pat. Off. |
| 0317957 | 11/1988 | European Pat. Off. |
| 0318948 | 6/1989 | European Pat. Off. |
| 0328147 | 8/1989 | European Pat. Off. |
| 0441218 | 8/1991 | European Pat. Off. |
| 2172594 | 9/1986 | United Kingdom. |
| 9003188 | 4/1990 | WIPO. |

OTHER PUBLICATIONS

Borrebaeck, Journal of Immunological Methods, vol. 123, pp. 157–165 (1989).

Hermentin et al., Behring Inst. Mitt. No.82, pp. 197–215 (1988).

J. Gallego et al., "Preparation of Four Daunomycin-Monoclonal Antibody 791T/36 Conjugates with Anti-Tumor Activity", Int. J. Cancer, vol. 33, pp. 737–744, (1984).

File Serveur STN Karlsruhe, File Chemical Abstracts, vol. 94, No. 7 (Columbus, Ohio, US), S. Isoda, et al.: "Medicinal chemcial studies in antiplasmin drugs. VII. Oxa analogs of 4-aminomethylcyclohexane ecarboxylic acid", see abstract No. 47233j, & Chem. Pharm. Bull., 28(8), 2329–36.

Journal of Controlled Release, vol. 9, No. 1, Jun. 1989, Elsevier Science Publishers B.V., (Amsterdam, NL), B. Rihova et al.: "Action of polymeric prodrugs based on N-(2-hydroxypropyl)methacrylamide copolymers. I. Suppression of the antibody response and proliferation of mouse splenocytes in vitro", pp. 21–32.

Journal Med. Chem 1984, 27, 638–645, "Intensely Potent Morpholinyl Anthracyclines", Edward M. Acton, et al.

*Primary Examiner*—Ponnathapura Achutamurthy
*Attorney, Agent, or Firm*—Oblon, Spivak, McClelland, Maier & Neustadt, P.C.

[57] ABSTRACT

The present invention provides anthracycline conjugates with carriers such as monoclonal polyclonal antibodies, proteins or peptides, or other synthetic carriers. These anthracycline conjugates provide pharmaceutical compositions which are useful for treating certain mammalian tumors. The compounds of the present invention have higher potency than anthracyclines, and improved therapeutic efficacy and reduced toxic effects.

6 Claims, 3 Drawing Sheets

ANTHRACYCLINE-CONJUGATES

This application is a Continuation of application Ser. No. 07/917,064, filed on Aug. 5, 1992, now abandoned, which was filed as International Application No. PCT/EP91/02284, on Dec. 3, 1991.

BACKGROUND OF THE INVENTION

Field of the Invention

The present invention relates to conjugates of therapeutically useful anthracyclines with carriers such as polyclonal and monoclonal antibodies or proteins or peptides of natural or synthetic origin; methods for their preparation, pharmaceutical composition containing them and use thereof in treating certain mammalian tumors. The invention also relates to new anthracycline derivatives and their preparation.

DISCUSSION OF THE BACKGROUND

In the last years, many highly cytotoxic anthracyclines have been synthesized. For example, those bearing a morpholino or morpholino substituted ring linked at C-3' position of the sugar moiety have shown promising antitumor activity on experimental murine tumors [see: Bioactive molecules, 55–101, vol 6. Edited by J. William Lown, Elveiser 1988].

SUMMARY OF THE INVENTION

The scope of the present invention is to provide anthracycline conjugates with carriers such as monoclonal or polyclonal antibodies or proteins or peptides or other carriers of synthetic origin in order to take advantage of the high potency of the anthracyclines, for example the morpholino derivatives, to improve their therapeutic efficacy and to reduce their toxic effects.

The conjugates of the present invention, characterized by the presence of an acid sensitive acetalic bond, have general formula 1

[A—O—W—Z]$_a$—T    1 wherein the moiety A—O— is the residue of any anthracycline of formula A—O—H bearing at least one primary or secondary hydroxyl group; a is an integer of from 1 to 30; W is a residue of formula 2

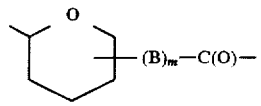

wherein B represents a $C_1$–$C_6$ alkylene group optionally hetero interrupted and m is 0 or 1; a $C_1$–$C_6$ alkylene group may be a $C_1$–$C_6$ alkylene group such as methylene, ethylene, ethylidene or n-propylene. The heteroatom interrupting the alkylene group may be oxygen or nitrogen. Preferably B represents —$CH_2$—O—$CH_2$—, —$CH_2$—NH—$CH_2$—, —$CH_2$—, —$C_3H_6$— or —$C_6H_{12}$—; Z is a spacer group and T is a carrier moiety. Preferred Z groups are: i) —NH—, and T—Z represents the residue of a carrier of formula T—$NH_2$ bearing at least one free amino group, or ii) —NH—[D]d—N=CH— wherein d is an integer of from 0 to 2, [D] represents —NH—CO($CH_2$)$_n$CO—NH— (n is 2 or 4) and T—Z comprises the residue of a carrier of formula T—CHO bearing at least one formyl group or T—[COOH] in which a is as defined above, iii) the piperazinylcarbonyl moiety or a group of formula —NH—[D]d—NH—CO— wherein [D] and d are as defined above and T—Z comprises the residue of a carrier of formula T—[COOH]$_a$ in which a is as above defined.

In the above formula 1 the anthracycline glycoside A—O—H is preferably derived from compounds of formula 3:

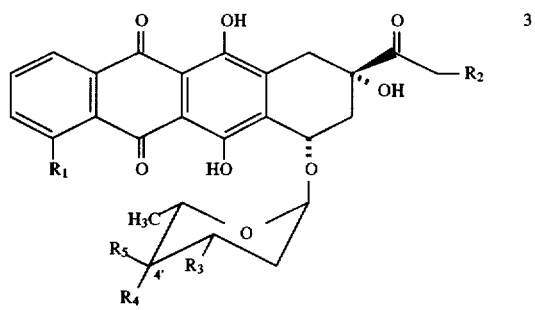

in which: $R_1$ is a hydrogen atom, a hydroxy or a methoxy group; a) $R_2$ is a hydroxy group and $R_4$ or $R_5$ is a hydrogen atom and the other of $R_4$ and $R_5$ is a hydroxy group or, $R_4$ is a iodine atom and $R_5$ is a hydrogen atom or both $R_4$ and $R_5$ are hydrogen atoms or b) $R_2$ is a hydrogen atom and $R_4$ or $R_5$ represents a hydroxy group and the other of $R_4$ and $R_5$ is a hydrogen atom; and $R_3$ is an amino group or represents a nitrogen atom enclosed in a morpholino (MO) or 3-cyano-4-morpholino (CM) or 2-methoxy-4-morpholino (MM) ring in which the nitrogen atom is linked at C-3

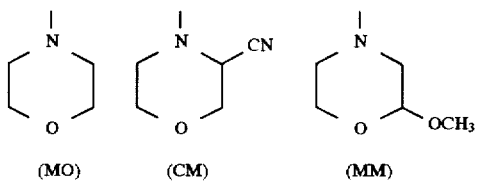

(MO)    (CM)    (MM)

The anthracycline may be linker to the carrier via the hydroxyl group at the C-14 or C-4'-position of the anthracycline compound. In one embodiment, carrier linked to the anthracycline at position C-14, formula 3' represents the moiety A—O—:

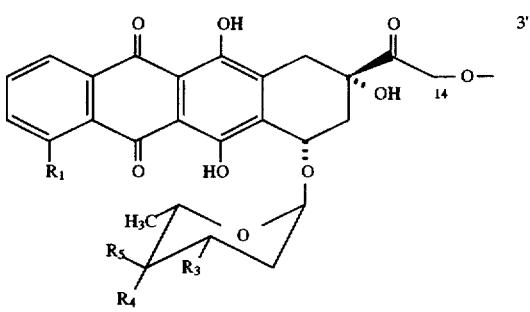

in which $R_1$ and $R_2$ are as defined above and $R_4$ or $R_5$ is a hydrogen atom and the other of $R_4$ and $R_5$ is a hydroxy group or $R_4$ is a hydrogen or iodine atom and $R_5$ is a hydrogen atom.

In another embodiment, carrier linked to the anthracycline via the hydroxy group at C-4', formula 3" represents the moiety A—O—:

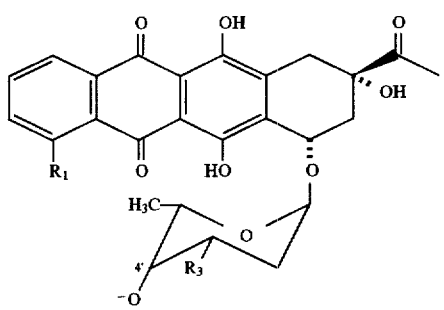

in which $R_1$ and $R_3$ are as defined above.

The carrier is typically selected from a polyclonal antibody, or fragment thereof comprising an antigen binding site, capable of binding to a tumor associated antigen; a monoclonal antibody, or fragment thereof comprising an antigen binding site, capable of binding to an antigen preferentially or selectively expressed on tumor cell populations; a peptide or protein capable of preferentially or selectively binding to a tumor cell; and a polymeric carrier.

The carrier portion T—$NH_2$ or T—[COOH]$_a$ of the conjugates is therefore preferably derived from polyclonal antibodies raised against tumor associated antigens; or from monoclonal antibodies binding to antigens preferentially or selectively espressed on tumor cell populations; or from natural or recombinant peptides or proteins or growth factors preferentially or selectively binding to tumor cells; or from natural or synthetic polymeric carriers such as polylysine, polyglutamic acid, polyaspartic acid and their analogues and derivatives, or such as dextran or other polymeric carbohydrate analogues and their derivatives; or from synthetic copolymers such as those derived from N-(2-hydroxypropyl)methacrylamide (HPMA) [see: J. Kopecek, Macromolecules. H. Benoit & P. Rempp, Ed.: 505–520 (1982) Pergamon Press, Oxford, England]; or from poly (aminoacid) copolymers such as poly(GluNa, Ala, Tyr) which are useful as targetable drug-carriers for lung tissue [R. Duncan et al., Journal of Bioactive and Compatible Polymers, Vol 4, July 1989]. The carrier portion may be also derived from portions of the above mentioned carriers, such as the Fab or the F(ab')$_2$ fragments of the antibodies, or such as portions of the above mentioned peptides or proteins obtained through recombinant DNA techniques.

Representative examples of the above mentioned antibodies and of respective possible therapeutic applications are:

-anti T-cell antibody T101 [Royston, I. et al., J. Immunol. 1980, 125, 725]
-anti CD5 antibody OKT1 (Ortho) ATCC CRL 8000 (cronic lymphocitic leukemias)
-anti trasferrin receptor antibody OKT9 (Ortho) ATCC CRL 8021 (ovaric and other tumors)
-anti melanoma antibody MAb 9.2.27 (Bumol, T. F. et al., Proc. Natl. Acad. Sci. USA 1982, 79, 1245) (melanomas)
-anti carcinoma markers antibody such as:
 -anti-CEA 1116 NS-3d ARCC CRL 8019
 -anti alpha-fetoprotein OM 3-1.1 ATCC HB 134 (also hepatomas)
 -791T/36 [Embleton, M. J. et al., Br. J. Cancer 1981, 43, 582] (also osteogenic sarcoma)
 -B 72.3 [U.S. Pat. No. 4,522,918 (1985)] (colorectal carcinomas and other tumors)
-anti ovarian carcinoma antibody OVB 3 ATCC HB 9147
-anti breast carcinoma antibody (HMGF antigen) [Aboud-Pirak, E. et al., Cancer Res. 1988, 48, 3188]
-anti bladder carcinoma 1G3.10 [Yu, D. S. et al., Eur. J. Urol. 1987, 13, 198]

Representative examples of the above mentioned growth factors and proteins of natural or recombinant origin are FGF, EGF, PDGF, TGF-α, α-MS, Interleukines, Interferones, TNF, melanotropin (MSH), etc. The carrier T—CHO is preferably derived from polyclonal or monoclonal antibodies having the carbohydrate moiety, preferentially located in the Fc region, selectively oxidized to aldehyde groups by means of chemical or enzymatic methods, as described in U.S. Pat. No. 4,671,958 (Jun. 9, 1987). The carrier T—CHO may be also derived from the formylation or from the oxidation of suitable polymeric carriers, or from the oxidation to aldehyde groups of the carbohydrate residues of suitable glycoproteins.

The invention further provides a method for preparing a compound of formula 1 which comprises: a) converting a derivative of formula 4:

$$A^1\text{—O—W—OH} \qquad 4$$

wherein $A^1$—O— is the residue of any anthracycline bearing at least one primary or secondary hydroxyl group and having the amino group of the sugar moiety protected or replaced by a morpholino derivative and W is as above defined, into an activated derivative of the formula 5:

$$A^1\text{—O—W—L} \qquad 5$$

wherein $A^1$—O— and W have the same meanings as above defined and L represents an activating group for making an amidic linkage such as N-oxysuccinimido, N-oxysulfosuccinimido or 2,4-dinitrophenoxy or 2,3,4,5,6-pentafluorophenoxy or t-butoxy carbonyloxy; and b) (i) condensing the resultant compounds of formula 5, as above defined, with a compound of formula T—$NH_2$ as previously defined; or (ii) reacting the activated compound of formula 5 with a derivative of formula $NH_2$—[D]$_d$—$NH_2$ such as hydrazine (d=0) or succinic (d=1 and n=2) or adipic (d=1 and n=4) dihydrazide, optionally deprotecting the resultant derivative of formula 6:

$$A^1\text{—O—W—NH—[D]}_d\text{—NH}_2 \qquad 6$$

wherein $A^1$—O—, W, d and [D] are as above defined and condensing it with a compound of formula T—CHO or T—[COOH]$_a$ as previously defined or (iii) reacting the compound of formula 5 with 1,4-piperazine and condensing the resultant compound of formula 7:

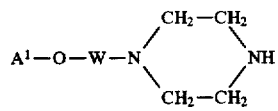

wherein $A^1$—O— and W are as above defined, with a compound of formula T[COOH]$_a$ as defined above, optionally in presence of a condensing agent to give conjugate of formula 1, in which the unreacted optionally present activated carboxyl groups may be quenched with a pharmaceutically acceptable amine.

For example, an activation method for the conversion of derivatives of formula 4 into N-oxysuccinimidyl derivatives of formula 5 in step (a) of the present process is the reaction of a derivative of formula 4 with N-hydroxysuccinimide or its water soluble 3-substituted sodium sulfonate salt in the presence of N,N'-dicyclohexyl-carbodiimide in a solvent such as ethyl acetate or N,N-dimethylformamide. In such a case in formula 5 —L represents the residue:

L = 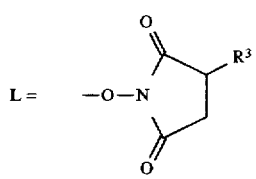

wherein $R_a$ represents hydrogen atom or sodium sulphate group.

The condensation methods for preparing conjugates of formula 1, starting from the above mentioned derivatives of formula 5 and a carrier of formula T—NH₂ are carried out in conditions capable of creating covalent linkages of amidic type and compatible with the structure of the carrier. Preferred conditions encompass use of buffered aqueous solutions at pH 7–9.5, temperatures of 4°–37° C., for times from some hours to several days.

For example, conditions for the condensation (b) (i) between the compounds of formula 5 and antibodies T—NH₂ are: aqueous 0.1M sodium phosphate and aqueous 0.1M sodium chloride at pH 8 containing a monoclonal antibody at 1 mg/ml, treated with a 30 fold molar excess of a 10% w/v solution of 6 in N,N-dimethylformamide, for 24 hours at 20° C. The conjugate is purified by gel filtration on a SEPHADEX G-25 column (Pharmacia Fine Chemical, Piscataway, N.J.), eluting with PBS (phosphate-buffered saline).

Methods for preparing conjugates of formula 1, condensing the above mentioned derivatives 6 with a carrier of formula T—CHO, are carried out in conditions capable of creating covalent linkages of hydrazone type and compatible with the structure of the carrier. Preferred conditions encompass use of buffered aqueous solutions at pH 4–7.5, temperature of 4°–37° C., for times from some hours to several days.

Conditions for the coupling (b) (ii) between the compounds of formula 6 and antibodies T—CHO are: aqueous 0.1M sodium acetate and aqueous 0.1M sodium chloride at pH 6 containing a monoclonal antibody at 1 mg/ml, treated with a 30 fold molar excess of a 5% w/v solution of 8 in the same buffer, for 24 hours at 20° C. The conjugate is purified by gel filtration as above described.

Method for preparing conjugate of formula 1, by condensing the above mentioned derivatives 6 or 7 and a carrier of formula T|COOH|$_a$ are carried out in conditions capable of creating covalent linkages of amidic type and compatible with the structure of the carrier.

Preferred conditions encompass use of buffered aqueous solutions at pH 7–9.5, temperature of 4°–37° C., for times from some hours to several days. Other conditions encompass use of dry dimethylformamide or dimethylsulfoxide at room temperature for 1 to 3 hours. Preferred conditions for the condensation between compounds of formula 6 or 7 and an activated carrier of formula T|CO—E|$_a$ in which E represents a suitable activating carbonyl group such as p-nitrophenil, are dry polar solvent such as dimethylformamide containing 5 to 50 mg/ml of compound 6 or 7 treated with an equivalent amount of compound T|CO—E|$_a$ for 1 to 24 hours at room temperature. Herein, the period "from some hours to several days" may be 4 hours to 5 days.

The derivatives of general formula 4, 5, 6, and 7 and their preparation are novel and are within the scope of the present invention. The compounds 4, 5, 6, and 7 are both useful intermediates and/or therapeutically active antitumor agents. The derivatives of formula 4 are prepared by a process which comprises:

(a) condensing an optionally protected anthracycline of the formula A—O—H as defined above, with the proviso that the amino group of the sugar moiety of the anthracycline A—O—H is in the form of a protected amino group, with a dihydropyran carboxylic derivative of formula 8:

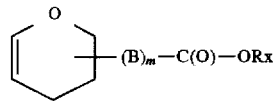

wherein B and m are as defined above and Rx is a protecting group;

(b) removing the or each protecting groups from the resultant intermediates, thereby to form a derivative of formula 4':

$$A—O—W—OH \qquad 4'$$

wherein W is as defined above with the proviso that the amino group of the sugar moiety of the anthracycline residue A—O— is in the form of a free amino group; and (c) (i) converting the free amino group of the sugar moiety of the anthracycline of formula 4' into a morpholino derivative or (ii) protecting the said free amino group of the said anthracycline of formula 4'.

The intermediate derivative of formula 4' and its preparation are also novel and form part of the present invention. The derivatives are both useful intermediates and/or therapeutically active antitumor agents. The conversion of anthracyclines of general formula A—O—H, suitably protected, into derivatives of general formula 4 as above defined, may be carried out by treatment with a compound of the formula 8 above defined.

The invention further provides a process for the preparation of a derivative of formula 4', which process comprises:

(a) condensing an optionally protected anthracycline of the formula A—O—H as defined above, with the proviso that the amino group of the sugar moiety of the anthracycline A—O—H is in the form of protected amino group, with a dihydropyran carboxylic derivative of formula 8 as defined above; and (b) removing the or each protecting group from the resultant intermediate.

Preferred conditions for carrying out the reaction of typically protected anthracyclines A—O—H, with compound 8 encompass the use of a sulfonic acid such as p-toluensulfonicacid as catalyst, in anhydrous apolar solvent such as methylene chloride, at room temperature for times from some hours to one day followed by mild alkaline treatment for deblocking the protecting groups.

Derivatives 8 are an enantiomeric mixture. However the etherification reaction with the hydroxyl group of anthracyclines, carried out with acid catalyst, gives only two diastereoisomers, indicated as x and y, having the ring undefined configuration (R or S) both at the acetalic C-2" position and at another position bearing the -(B)$_m$-C(O)ORx group.

The resulting compound of the formula A—O—W—ORx is converted into compound of the formula 4 as defined above by hydrolysis and deprotection. Some of the starting compound of the formula 8 are new and are within the scope of the present invention. Preferred derivatives of formula 8 comprise: 8A) 2-ethoxycarbonyl-3,4-dihydro-2H-pyran [m=0, Rx=C₂H₅] 8B) ethyl 2-(3,4-dihydro-2H-pyran-2-yl) methyloxyacetate [B=CH₂—O—CH₂, m=1, Rx=C₂H₅] 8C) methyl 2-(3,4-dihydro-2H-pyran-2-yl)methyloxyacetate [B=CH₂—O—CH₂, m=1, Rx=CH₃] 8D) ethyl 2-(3,4- dihydro-2H-pyran-2-yl)methylthioacetate [B=CH$_2$—S—CH$_2$, m=1, Rx=C$_2$H$_5$] 8E) ethyl 2-(3,4-dihydro-2H-pyran-2-yl)methylaminoacetate [B=CH$_2$—NH—CH$_2$, m=1, Rx=C$_2$H$_5$]

Compounds of general formula 8 can be prepared in several ways. For example, they may prepared readily starting from the available 3,4-dihydro-2H-pyran-2-carboxylic acid, sodium salt [CAS 16698-52-5] of formula H or from the corresponding methanol derivative [CAS 3749-36-8] of formula M:

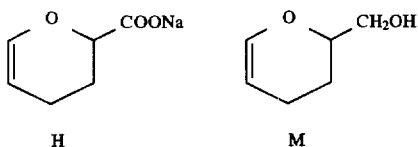

More particularly, compound 8A is prepared by reacting compound H with ethyl iodide in an anhydrous polar solvent, such as dimethylformamide, as described in "Macromolecules" Vol 12, No 1, p 5–9, Jan.–Feb. 1979. The methyloxyacetate 8B can be prepared by reacting the alcohol M with chloroacetic acid in dry dimethylformamide at 100° C. in the presence od two equivalents of sodium or potassium hydroxide, then cooling the mixture and treating it with ethyl iodide.

Compounds of formula 8C–E can be prepared by Wurz condensation of the iodo derivative of M, prepared by displacement of a sulfonic ester of M with sodium iodide, and ethyl 3-iodopropionate, ethyl 4-iodobutanoate or ethyl 7-iodoheptanoate. The methylaminoacetate 8F is prepared by refluxing a sulfonic ester of alcohol M with ethyl glycine in dry toluene for six hours.

Starting anthracyclines of formula 3 for use in the present invention include those bearing a free hydroxyl group, at position C-4' or C-14, such as: daunorubicin (3a: R$_1$=OCH$_3$, R$_2$=R$_5$=H, R$_3$=NH$_2$, R$_4$=OH) 4-demethoxydaunorubicin (3b: R$_1$=R$_2$=R$_5$=H, R$_3$=NH$_2$, R$_4$=OH) 4'-epidaunorubicin (3c: R$_1$=OCH$_3$, R$_2$=R$_4$=H, R$_3$=NH$_2$, R$_5$=OH) 4'-deoxydoxorubicin (3d: R$_1$=OCH$_3$, R$_2$=OH, R$_4$=R$_5$=H, R$_3$=NH$_2$) 4'-deoxy-4'-jododoxorubicin (3e: R$_1$=OCH$_3$, R$_2$=OH, R$_5$=H, R$_4$=J, R$_3$=NH$_2$) and those bearing both secondary and primary hydroxy groups such as: doxorubicin (3f: R$_1$=OCH$_3$, R$_2$=R$_4$=OH, R$_5$=H, R$_3$=NH$_2$) 4'-epidoxorubicin (3g: R$_1$=OCH$_3$, R$_2$=R$_5$=OH, R$_4$=H, R$_3$=NH$_2$), all disclosed in previous patents see: F. Arcamone "DOXORUBICIN" Medicinal Chemistry vol 17, New York, N.Y. 1981.

For example, antracyclines originally bearing a hydroxyl group, for instances those represented by compounds 3a–e, are converted into their N-trifluoroacetyl analogues then reacted with a dihydropyrancarboxylic ester derivatives of general formula 8, as previously described, to afford compounds 4(a–e)(A–Z) in which (a–e) indicate the residue of anthracyclines of formula 3"(a–e) and 3'(d), (A–Z) indicates the residue of general formula 2 derived by condensing a compound of formula 8 to the hydroxyl group at C-4' or at C-14 of the anthracycline.

Anthracyclines bearing both hydroxyl groups at C-4' and C-14 positions, for instances those represented by compounds 3(f,g), may be selectively condensed at C-14 hydroxyl group with compounds of formula 8, after temporary protection of the other hydroxyl group at C-4', to give derivatives of general formula 4 and 4', indicated as 4(f,g) (A–Z) and 4'(f,g)(A–Z), in which (f,g) indicates the residue of anthracycline of formula 3'(f,g) (pyranylation at C-14) or 3"(f,g) (pyranylation at C-4') and (A–Z) have the same meaning as above reported.

Derivatives 4 and 4', as above reported, in which residue —O—W is linked at C-14 hydroxy position are prepared by reacting a compound of formula 8, in the same conditions as previously described, with anthracycline derivative bearing protected C-4'hydroxyl group of general formula 9

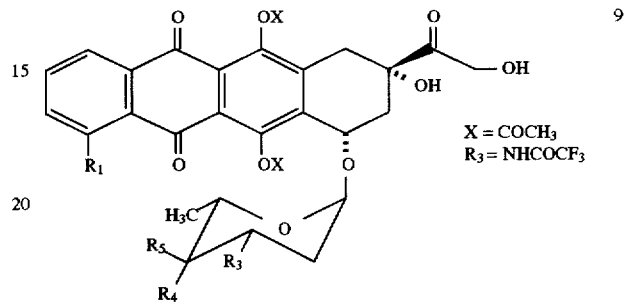

wherein R$_1$ has the same meaning above reported, R$_4$ or R$_5$ is acethoxy group and the other of R$_4$ and R$_5$ is hydrogen atom.

For example, N-trifluoroacetyl derivatives of general formula 3 (R$_3$=NHCOCF$_3$), such as 3(f,g) are first protected at C-9 and C-14 as 9,14-ethylorthoformate upon reaction with triethyl orthoformate following the procedure described by H. Umezawa et al., J. Antib, vol XXXIII No.12, 1581 (1980), then acylated at phenolic and C-4' hydroxyl groups by using acetic anhydride and pyridine and subsequently deblocked at C-14 hydroxyl position by means of aqueous hydrochloric acid to afford 6,11,4'-tri-O-acetyl-N-trifluoroacetyl doxorubicin derivatives of formula 9 which are condensed with a compound of formula 8 in the same conditions as above reported, to obtain, after deblocking of the phenolic groups by means of morpholine in methanol and deblocking of the hydoxyl group at C-4' with sodium methylate in methanol, compound 10. Finally, treatment of compound 10 with aqueous 0.1N sodium hydroxide affords derivative 4'. The process is illustrated in Scheme I.

Scheme I

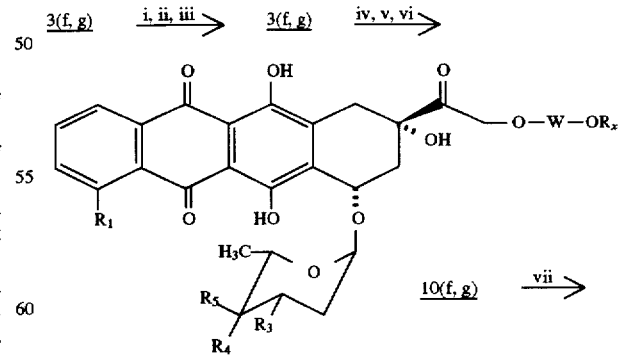

-continued
Scheme I

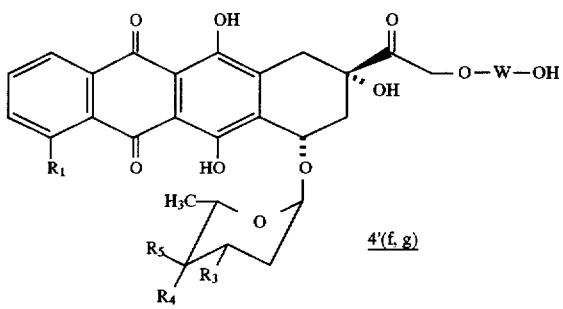

$R_3 = NHCOCF_3$;
$R_4 = H$ and $R_5 = OH$ or $R_4 = OH$ and $R_5 = H$

Reagents & Conditions:
i: $CH(C_2H_5O)_3$, pTSA, $CH_2Cl_2$; ii: $(CH_3CO)_2O$, pyridine; iii: 0.1N HCl—THF; iv: 8. pTSA, $CH_2Cl_2$, v: morpholine, $CH_3OH$: vi: $NaOCH_3$, $CH_3OH$; vii: 0.1N NaOH.

Another aspect of the present invention provides the preparation of morpholino (MO) and morpholino derivative (CM) and (MM) of general formula 4(MO), 4(CM) and 4(MM) from the derivatives of general formula 4' ($R_3=NH_2$), substituted at C-4' or C-14 prepared as above reported, following standard procedures described in previous patents.

More particularly, preparation of 4-morpholino 4(a-g) (A-Z)(MO) and 3-cyano-4-morpholino 4(a-g)(A-Z)(CM) compounds follows the procedure described by E. M. Acton et al., in J. Med. Chem. 1984, 27 638; 2-methoxy-4-morpholino derivatives 4(a-g)(A-Z)(MM) are prepared following the procedure described in U.S. Pat. No. 4,672,057 Jun. 9, 1987. It should be stressed that the residue —W, in compounds of formula 4'(a-g)(A-Z) does not interfere with the preparation of the above mentioned morpholino derivatives.

According to the process for preparing morpholino derivatives (MO), compounds 4'(a-g)(A-Z), dissolved in water, are first reacted with 2-oxyethyl-dihaldehyde (11),

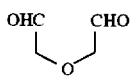

then with sodium cyanoborohydride to afford the morpholino derivative.

By changing the reaction conditions of the cyanoborohydride reduction, for instance by adding sodium cyanide, cyanomorpholino derivative (CN) are recovered.

Preparation of 2-methoxy-4-morpholino derivatives (MM) are performed by treating compounds 4'(a-g)(A-Z), dissolved in water, with 1-methoxy-2,2'-oxydiacetaldehyde (12)

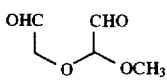

then with sodium cyanoborohydride.

The conjugates of formula 1 of the present invention are useful therapeutic agents since they contain an acetalic bond which releases the parent drug A—O—H upon hydronium-ion-catalyzed hydrolysis or "in vivo" enzymatic cleaveage.

It is well known that in malignant tumors there is a high rate of glycolysis compared to normal tissue. This causes an increase in the production of lactate and thus a decrease of the pH in the tumor [see: H. M. Rauen et al., Z. Naturforsch. Teil B, 23 (1968) 1461]. Also compounds of formula 4, 4', 6 and 7 may release the cytotoxic anthracycline within tumor tissues.

The invention affords a two level specificity of action of the compounds, the first one consisting in a preferential localization of the conjugate in the tumor tissue by means of antigenic recognition, and the second one consisting in a preferential release of the drug in its active form in the tumor tissue by means of preferential acidic cleavage.

The conjugates produced according to the methods described are characterized following different chemico-physical methods.

The retention of the original molecular weight and the lack of aggregate formation is assessed by chromatographic gel filtration procedures (Yu, D. S. et al., J. Urol. 140, 415, 1988) with simultaneous and independent detection of anthracycline and antibody at different wavelengths, and by gel electrophoretic methods.

The overall charge distribution of the compounds obtained is assessed by chromatographic ion exchange methods.

The anthracycline concentration is assessed by spectrophotometric titration against a standard calibration curve obtained from the parent anthracycline.

The protein concentration is assessed by colorimetric assays such as the bicinconic acid assay (Smith, P. K. et al., Anal. Biochem. 150, 76, 1985) or the Bradford dye assay (Bradford, M. M., Anal. Biochem. 72, 248, 1976).

The antigen binding activity retention of the antibodies, after the conjugation procedures, is assessed by an ELISA method (Yu, D. S. et al., J. Urol. 140, 415, 1988) and by cytofluorimetric methods (Gallego, J. et al., Int. J. Cancer 33, 737, 1984).

The evalutation of the retention of cytotoxicity of conjugates in comparison with the parent drug is assessed by a test of inhibition of uptake of $^3$H-Thymidine by the target cells, after an incubation time long enough to explicate the maximum cytotoxic effect (Dillmann, R. O. et al., Cancer Res. 48, 6097, 1988).

The evalutation of selective cytotoxicity of the conjugates toward an antigen positive in comparison with an antigen negative cell line is assessed by a test of inhibition of uptake of $^3$H-Thymidine by antigen positive vs. antigen negative cell lines, after a short incubation time (Dillmann, R. O. et al., Cancer Res. 48, 6096, 1988).

The acid sensitivity of the conjugate is evaluated by the above mentioned chromatographic methods after incubation of the compounds in suitable buffered solutions.

Alternatively, radiolabelling of the conjugates in the antibody moiety ($^{125}$I) and/or in the anthracycline moiety ($^{14}$C) and HPLC analytical methods are employed for the evalutation of stability in plasma.

The therapeutic effect of the compounds and the improvement of their therapeutic efficacy in comparison with the parent drug, are assessed in animal models of human transplanted tumors. Nude mice bearing xenografts of human tumors are treated with suitable doses of conjugates, of free drug, of antibody, and of a physical mixture of drug and antibody, at equivalent doses, and the tumor growth is recorded and compared in the different treatment groups.

The immunoglobulin conjugates are formulated as pharmaceutical compositions with a pharmaceutically acceptable carrier or diluent. Any appropriate carrier or diluent may be used. Suitable carriers and diluents include physiological saline solution and Ringers dextrose solutions.

The conjugates of the invention are useful as antitumor agents. A mammal, e.g. a human or animal, may therefore be treated by a method comprising administering thereto a pharmaceutically effective amount of a conjugate of formula 1 as hereinbefore defined. The condition of the human or animal may be ameliorated or improved in this way.

TLC chromatography are performed with KIESELGEL plates Merck $F_{254}$ using the following eluting systems (v/v): system A: methylene chloride:methanol (98:2) system B: methylene chloride:methanol:acetic acid:water (80:20:7:3) system C: methylene chloride:methanol (95:5) system D: methylene chloride:acetone (4:1) system E: methylene chloride:methanol:acetic acid (80:20:1) system F: methylene chloride:acetone (9:1) system G: methylene chloride:acetone (95:5) system H: methylene chloride:methanol (90:10)

BRIEF DESCRIPTION OF THE DRAWINGS

The invention is further illustrated by the accompanying drawings, in which.

BRIEF DESCRIPTION OF THE PREFERRED EMBODIMENTS

Figure 1:
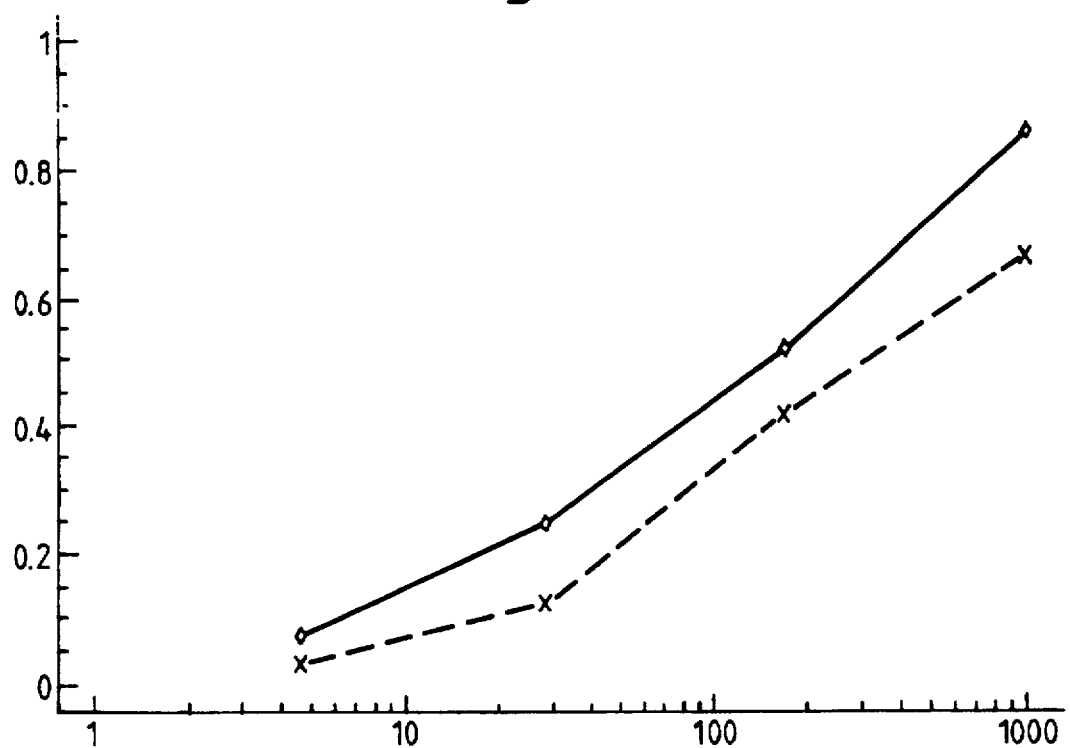
FIG. 1 is a graph showing the results of an ELISA, reported in Example 30 which follows, to evaluate the binding to a human melanoma cell line of an anti-transferrin receptor immunoconjugate of the invention $1^3$ (line X—X—X), and of the parent anti-human transferrin receptor antibody OKT9 (line ◊—◊—◊). In the graph optical absorbance at 495 nm (y axis) is plotted against antibody concentration in ng/ml.

The following Examples illustrate the invention.

Example 1

Preparation of Ethyl 2-(3,4-dihydro-2H-pyran-2-yl) methyloxyacetate (8B)

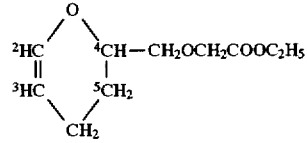

2-methanol-3,4-dihydro-2H-pyran (formula M, 4.2 g, 35 mmol), dissolved in anhydrous methanol (100 ml), was added with sodium hydroxyde (1.6 g, 40 mmol) and gently warmed. Then the solvent was removed in vacuo and the residue was dissolved with dimethylsulfoxide (100 ml). To this solution, warmed at 100° C., was added 2-chlorosodium acetate (6 g, 1.5 mmol) in dimethylsulfoxide (100 ml) within 2 hours under vigorous stirring. After standing for half an hour, the reaction mixture was cooled, added with triethylamine (5 ml) and ethyl jodide (5 ml) and kept at room temperature overnight. Then the reaction mixture was diluted with water and extracted with ethyl ether. After standard work up, the title compound was purified by chromatography on silicic acid eluting with a mixture of petroleum ether-ether (80:10 v/v). 1.68 g of compound 5 was recovered as an oil, yield 26%. TLC on KIESELGEL plate $F_{254}$ (Merck) using as eluting system the mixture petroleum ether:ether 1:1 by volume) $R_f$=0.7 $^1$HNMR (200 MHz, $CDCl_3$) δ: 1.26 (t, J=7.1 Hz, 3H, $CH_2CH_3$); 1.6–2.2 (m, 4H, $CH_2$-3, $CH_2$-4); 3.64 (d, J=5.2 Hz, 2H, $CH_2O$); 4.00 (m, 1H, H-2); 4.13 (m, 2H, $OCH_2C=O$); 4.19 (q, J=7.1 Hz, 2H, $CH_2CH_3$); 4.65 (m, 1H, H-5); 6.35 (ddd, J=6.2, 2.0, 2.0 Hz, 1H, H-6).

Example 2

Preparation of 4'-epi-4'-O-(2-carboxytetrahydropyran-6-yl) daunorubicin: x and y isomers (2"R,6"R and 2"S,6"S).

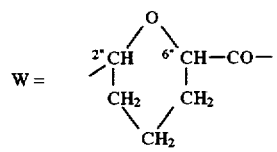

4'-epi-N-trifluoroacetyldaunorubicin (3c: $R_3$=NHCOCF$_3$) (3.1 g, 5 mmole) was dissolved in anhydrous methylene chloride (500 ml) and treated with 3,4-dihydro-2H-pyran-2-ethoxycarbonyl (8A, 3.4 g, 25 mmole), prepared as described in "Macromulecules" Vol 12, No 1, p 5–9, Jan.–Feb. 1979, and p-toluensulfonic acid (100 mg) at room temperature under nitrogen. After one hour a chromatographic control showed the formation of two products having, respectively, $R_f$ value of 0.53 and 0.36 in system A. The reaction mixture was washed with aqueous solution of 5% sodium hydrogen carbonate and water, then the organic phase was separated off, dried over anhydrous sodium sulphate, concentrated to small volume under reduced pressure and chromatographed on silicic acid column to afford 4'-epi-4'-O-(2-carboethoxytetrahydropyran-6-yl)-6yl)-N-trifluoracetyl daunorubicin derivatives of the title compounds having respectively $R_f$ value of 0.53 (1.5 g, yield 40%) and 0.36 (1.28 g, yield 32%) in system A. Compound $R_f$=0.53; FD-MS: m/e 663 (M+) ¹HNMR (200 MHz, CDCl₃) inter alia δ: 1.31 (COOCH₂CH₃, J=7.1 Hz), 1.33 (5'-CH₃, J=6.4 Hz), 2.41 (COCH₃), 3.40 (4'-H, J=9.7 Hz), 4.07 (4-CH₃O), 4.55 (6"-H), 4.96 (2"-H), 5.30 (7-H), 5.48 (1"-H), 7.92 (NHCOCF₃) Compound $R_f$=0.36 FD-MS: m/e 663 (M+) ¹HNMR (200 MHz, CDCl₃) inter alia δ: 1.28 (COOCH₂CH₃, J=7.1 Hz), 1.38 (5'-CH₃, J=6.4 Hz), 2.42 (COCH₃), 3.54 (4'-H, J=8.7 Hz), 4.07 (4-CH₃O), 4.42 (6"-H), 5.10 (2"-H), 5.29 (7-H), 5.48 (1'-H), 6.62 (NHCOCF₃).

Compound $R_f$=0.53 (1.4 g, 1.79 mmole) was dissolved with aqueous 0.2N sodium hydroxide under nitrogen and kept at 0° C. for eight hours. Then the aqueous solution was adjusted to pH 3 with aqueous 1N hydrogen chloride and extracted repedetly with methylene chloride. The organic phase was washed with water, separated off, dried over anhydrous sodium sulphate and evaporated under reduced pressure to give x, one of the two isomers (x and y)) of the title compound 4'c(A), (0.9 g, yield 79%). $R_f$=0.60 (system B). FD-MS: m/e 639 (m+)

Compound $R_f$=0.36 (1.1 g, 1.4 mmole) was hydrolized as above described to give, after standard work up, the other isomer y of the title compound 4'c(A), (0.72 g, yield 80%). $R_f$=0.45 (system B). FD-MS: m/e 639 (M+).

Example 3

Preparation of 4'-epi-4'-O-(2-carboxytetrahydropyran-6 yl)-3'-deamino-3'(4-morpholino)daunorubicin: x isomer (one of the two 2"R,6"R or 2"S,6"S)

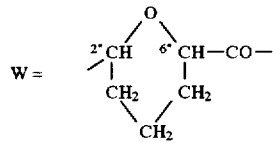

Compound 4'c(A) (x isomer) (1.2 g, 1.8 mmole) prepared as described in Example 2, was dissolved in water (200 ml), adjusted to pH 7.5 with hydrogen sodium carbonate and added with 2-oxyethyl-dihaldehyde (11, 3 g) dissolved in water (20 ml). After one hour a solution of sodium cyanoborohydride (100 mg) in water (6 ml) was added, under stirring at room temperature. After thirty minutes the reaction mixture was brought to pH 6 with an aqueous solution of 5% acetic acid and extracted with n-butylic alcohol. The organic phase was washed with water, and the solvent removed under reduced pressure. The residue was purified by chromatography on a column of silic acid using the system methylene chloride: methanol:acetic acid (90:8:2 by volume) to give, after standard work up, the title compound 4c(A)(MO) (0.6 g, yield 45%). $R_f$=0.70 (system B). FD-MS: m/e 724 (M+). ¹HNMR (200 MHz, CDCl₃) inter alia δ: 1.29 (5'-CH₃, J=6.3 Hz), 2.42 (COCH₃), 2.4–2.8 (CH₂—N—CH₂), 2.98 (3'-H), 3.65 (CH₂O-CH₂), 3.40 (4'-H, J=9.0 Hz), 4.08 (4-CH₃O), 4.30 (6"-H), 5.00 (2"-H), 5.27 (7-H), 5.51 (1'-H)

Example 4

Preparation of N-oxysuccinimidyl derivative of 4'-epi-4'-O-(2-carboxytetrahydropyran-6-yl)-3'-deamino-3'(4-morpholino) daunorubicin: x isomer (one of the two 2"R,6"R or 2"S,6"S)

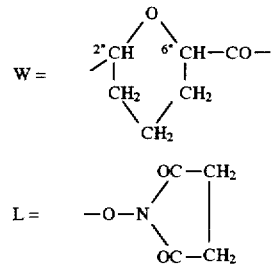

Compound 4c(A)(MO) (0.55 g, 0.7 mmole) prepared as described in Example 3, was dissolved in anhydrous dimethylformamide (25 ml) and treated with N-hydroxysuccinimide (95 mg) and N,N-dicyclohexylcarbodiimide (0.15 g). The mixture was kept at 4° C. for two days, then the solvent was removed under reduced pressure. The residue was picked up with little ethyl acetate, filtered off and the solvent removed under reduced pressure. This procedure was performed four times in order to remove the dicyclohexylurea. Finally, the residue was treated with ether from which crystallised 0.45 g, yield 72%, of pure title derivative 5c(A)(MO). $R_f$=0.45 (system B) FD-MS m/e 821 (M+) ¹HNMR (200 MHz, CDCl₃) inter alia δ: 2.42 (COCH₃), 2.4–2.6 (CH₂—N—CH₂), 2.82 (CO—CH₂—CH₂—CO), 3.5–3.7 (CH₂—O —CH₂), 4.08 (4-CH₃O), 5.13 (2"-H), 5.28 (7-H, 6"-H), 5.52 (1'-H).

Example 5

Preparation of 6,11,4'-tri-O-acetyl-N-trifluoroacetyl-doxorubicin (9f)

N-trifluoroacetyl-doxorubicin (3f: R₃=NHCOCF₃) (6.4 g, 10 mmole) was suspended in anhydrous methylene chloride (750 ml) and added with triethylorthoformate (150 ml) and p-toluensulfonic acid (3 g), under stirring at room temperature. After three hours a chromatographic control showed disappearance of the starting material. After standard work up with water, the organic phase was separated off, dryied over anhydrous sodium sulphate and filtered off. The solvent removed in vacuo to afford a crude product which was dissolved in a mixture of pyridine (50 ml) and acetic anhydryde (50 ml) and added with little dimethylaminopyridine (0.5 g). After two hours, the reaction mixture was poured in water and ice (2000 ml). The precipitate was collected on a sintered glass, washed with water, dissolved with tetrahydrofurane (400 ml) and treated with 0.1N aqueous hydrogen chloride (50 ml) overnight at room temperature. Then methylene chloride was added and the organic phase was washed with water, 5% aqueous sodium hydrogen carbonate, and twice with water. After usual work up, the residue was purified by chromatography on a column of silicic acid using the solvent system methylene chloride:acetone (90:10 by volume) to give 5 g, yield 65%, of the title compound 9f. $R_f$=0.18 (system D) FD-MS m/e 765 (M+) ¹HNMR (200 MHz, CDCl₃) δ: 1.20 (d, J=6.4 Hz, 3H, 5'-CH₃), 1.9–2.0 (m, 2H, 2'-CH₂), 2.1–2.4 (m, 2H, 8-CH₂), 2.19, 2.49, 2.53 (s, 9H, COCH₃ ×3), 2.95 (bt, J=4.2, 1H, CH₂—OH), 3.13 (bm, 2H, 10-CH₂), 3.99 (s, 3H, 4-CH₃O), 4.20 (q, J=6.6 Hz, 1H, 5'-H), 4.35 (m, 1H, 3'-H), 4.44 (bs, 1H, 9-OH), 4.74 (m, 2H, CH$_2$—OH), 5.1–5.3 (m, 3H, 7-H, 1'-H, 4'-H), 6.40 (bd, J=6.4 Hz, 1H, NH), 7.3–7.8 (m, 3H, 1-H, 2-H, 3-H).

Example 6

Preparation of 14-O-(2-carboxytetrahydropyra-6-yl) doxorubicin, x and y isomers (2"R,6"R and 2"S, 6"S).

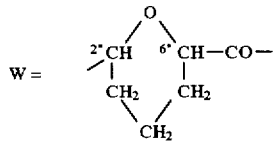

6,11,4'-tri-O-acetyl-N-trifluoroacetyldoxorubicin (10f) (5 g, 6.5 mmole), prepared as described in Example 5, was dissolved in anhydrous methylene chloride (600 ml) and treated with 2-ethoxycarbonyl-3,4-dihydro-2H-pyran (8A) (5 g, 36 mmole) and p-toluensulfonic acid (500 mg) at room temperature under nitrogen. After two hours the reaction mixture was washed with aqueous solution of 5% sodium hydrogen carbonate and water, then the organic phase was separated off, dried over anhydrous sodium sulphate, concentrated to small volume under reduced pressure and added with petroleum ether. The precipitate was dissolved in methanol (500 ml), added with morpholine (8 ml) and was kept at room temperature for two hours. After that, the reaction mixture was added with acetic acid (10 ml) and extracted with methylene chloride. The organic phase was concentrated to small volume and cromatographed on a silicic acid column using, as eluting system, a mixture of methylene chloride: acetone (95:5 by volume) to obtain the N-trifluoroacetyl 14-O-(2-carbonyltrahydropyran-6-yl) doxorubicin (10f) (4.2 g, yield 82%). R$_f$=0.41 (system D); FD-MS m/e 795 (M+) $^1$HNMR (200M, CDCl$_3$) inter alia δ: 1.3 (5'-CH$_3$, COOCH$_2$CH$_3$), 3.65 (4'-H, J=2.1 Hz), 4.08 (4-OCH$_3$), 4.21 (COOCH$_2$CH$_3$, J=7.0 Hz), 4.48 (6"-H), 4.88 (9-COCH$_2$-O), 5.04 (2"-H), 5.27 (7-H), 5.50 (1'-H), 6.69 (NH)

Compound 10f was dissolved at 0° C. with 0.1N sodium hydroxyde (500 ml) under nitrogen. After one hour the reaction mixture was brought to pH 6 with acetic acid, extracted with n-butanol and washed with water. The organic phase was separated off and the solvent was removed in vacuo. The residue was pick ed up with little methylene chloride and added with ether to give the title product 4'f(A) (x,y isomers), 2.9 g (yield 66%). R$_f$=0.5 (system B); FD-MS m/e 671 (M+).

Example 7

Preparation of 14-O-(2-carboxytetrahydropyran-6-yl)-3'-deamino-3'|2(S)-methoxy-4-morpholino] doxorubicin: x and y isomers (2"R,6"R and 2"S, 6"S)

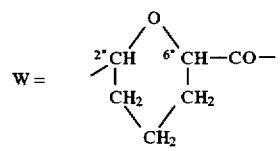

14-O-(2-carboxytetrahydropyran-6-yl)doxorubicin (4'f(A), 1.3 g, 2 mmole), prepared as described in Example 6, was dissolved in water (300 ml) and added with 1-methoxy-2, 2'-oxydiacetaldehyde (12) (3.4 g) dissolved in a mixture of acetonitrile (20 ml) and water (20 ml). The mixture was brought to pH 7.5–8.0 with triethylamine and left under stirring, at room temperature, for one hour. Then sodium cyanoborohydride (0.126 g), dissolved in water (10 ml), was added and the reaction mixture was kept at room temperature for 15 minutes. After that, acetone (10 ml) was added and the reaction mixture was added with little acedic acid and extracted with n-butanol. The organic phase was washed with water and the solvent was removed in vacuo. The residue was chromatographed on silicic acid column using as eluting solvent a mixture of methylene chloride:acetic acid:methanol (100:1:7 by volume). The title compound 4f(A)(MM) (0.30 g, yield 26%) was recovered after usual work up. R$_f$=0.8 (system E), FD-MS m/e 771 (M+) $^1$HNMR (200 MHz, CDCl$_3$) inter alia δ: 1.34 (5'-CH$_3$), 3.39 (CH$_3$—O "morpholino"), 4.07 (4-OCH$_3$), 4.47 (6"-H), 4.58 (CH—OCH$_3$ "morpholino"), 4.85 (9-COCH$_2$-O-), 5.04(2"-H), 5.27 (7-H), 5.59 (1'-H).

Example 8

Preparation of N-oxysuccinimidyl derivative of 14-O-(2-carboxytetrahydropyran-6-yl)-3'-deamino-3'|2(S)-methoxy-4-morpholino|doxorubicin: x and y isomers (2"R,6"R and 2"S,6"S).

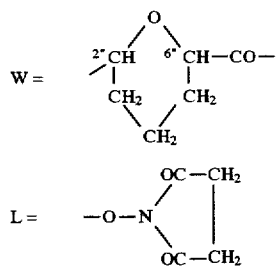

Compound 4f(A)(MM) (0.150 mg), prepared as described in Example 7, was dissolved in anhydrous dimethylformamide (25 ml) and treated with N-hydroxysuccinimide (95 mg) and N,N'-dicyclohexylcarbodiimide (0.15 g) following the procedure described in Example 4. The title compound 5f(A) (MM) was obtained with a yield of 85% (0.15 g). R$_f$=0.20 (system A); FD-MS m/e 868 (M+).

Example 9

Preparation of 14-O-(2-carboxymethyloxymethyl-tetrahydropyran-6-yl) doxorubicin: mixture of isomers 2"R,6"R; 2"S,6"S; 2"S,6"R; 2"R,6"S

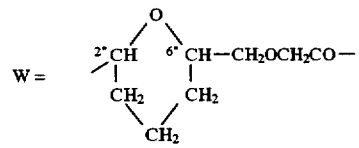

6,11,4'-tri-O-acetyl-N-trifluoroacetyl-doxorubicin (9f, 0.65 g, 0.85 mmol), prepared as described in Example 5, was dissolved in anhydrous methylene chloride (50 ml) and treated with compound 8B (0.7 g, 3.5 mmol) and anhydrous p-toluensulfonic acid (0.045 g) under nitrogen at room temperature. After 10 minutes, aqueous satured solution of sodium hydrogen carbonate (20 ml) was added. The organic phase was separated off and washed twice with water, dried over anhydrous sodium sulphate and the solvent was removed under reduced pressure. The oily residue was dissolved in methanol (50 ml) and treated first with morpholine (1.2 ml) for two hours, then with sodium methoxide (0.1 g) for half an hour. After that, the reaction mixture was brought to pH 7.5 with aqueous 0.1N hydrogen chloride and extracted with methylene chloride. After standard work up, the residue was chromatographed on silicic acid, using methylene chloride as aluting agent, to give 0.4 g (yield 56%) of a protected N-trifluoroacetyl and (2-ethyloxycarbonyl) derivative of the title product. $R_f$=31 (system D). FD-MS: m/e 839 (76, M+); 639 (84); 201 (100)

0.4 g (0.47 mmol) of N-trifluoroacetyl 2-ethyloxycarbonyl derivative above described, was treated with aqueous 0.1N sodium hydroxide (100 ml) at 0° C. under nitrogen for 90 minutes. After that, the solution was brought to pH 5 with acetic acid, extracted with water satured of n-butanol and washed with n-butanol satured of water. The solvent was removed under reduced pressure; the residue was piked up with a mixture of methylene chloride-methanol and the title product 4'f(B), 0.32 g (yield 94%), was precipitated by adding ethylic ether and collected on a sintered glass funnel. $R_f$=0.31 (system B). FD-MS: m/e 716 (23, MH+); 321 (100).

Example 10

Preparation of 14-O-(2-carboxymethyloxymethyl-tetrahydro-pyran-6-yl)-3'-deamino-3'(4-morpholino) doxorubicin: mixture of isomers 2"R,6"R; 2"S,6"S; 2"S,6"R; 2"R,6"S

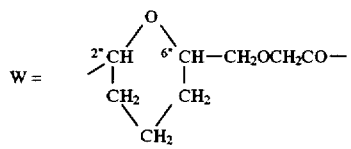

Product 4'f(B) (0.3 g) was dissolved in dry dimethylformamide (40 ml) and treated with triethylamine (0.3 ml) and bis(2-jodoethylether) (11, 2 ml) at 4°-5° C. After 24 hours, the solution was acidified with acetic acid and the solvent was removed under reduced pressure. The residue was treated with aqueos 0.1N sodium hydroxide at 0° C. under nitrogen. After 20 minutes, the solution was acidified with acetic acid and extracted with n-butanol, washed with water. The solvent was removed under reduced pressure and the crude material was purified on a silicic acid column eluting with a mixture of methylene chloride/methanol (90:5 by volume) to give the title compound 4f(B)(MO) (0.05 g, yield 23%). $R_f$=0.48 (system B) FAB-MS: 757 (M+)

Example 11

Preparation of N-oxysuccinimidyl derivative of 14-O-[2-carboxymethyloxymethyl-tetrahydropyran-6-yl]-3'-deamino-3'(4-morpholino)doxorubicin Mixture of isomers 2"R,6"R; 2"S,6"S; 2"S,6"R; 2"R,6"S

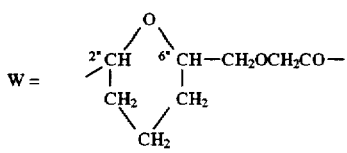

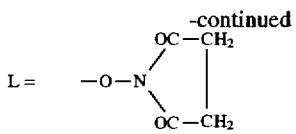

Product 4f(B)(MO) (0.03 g, 0.037 mmole) was dissolved in dry dimethylformamide (3 ml) and added with N-hydroxysuccinimide (0.01 g) and dicyclohexylcarbodiimide (0.02 g). The mixture was kept at room temperature for eight hours, after that, the solvent was removed in vacuo and the residue was chromatographed on silicic acid column using methylene chloride:methanol (95:5) as eluent, to give the title compound 5f(B)(MO) (0.028 g, yield 85%). $R_f$=0.52 (system H). FAB-MS: 852 (13, MH+); 200 (100)

Example 12

Preparation of 14-O-(2-carboxymethyloxymethyl-tetrahydro-pyran-6-yl)-3'-deamino-3'|2(S)-methoxy-4-morpholino|doxorubicin Mixture of isomers 2"R,6"R; 2"S,6"S; 2"S,6"R; 2"R,6"S

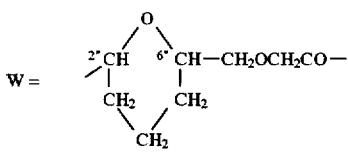

14-O-(2-carboxymethyloxymethyl-tetrahydropyran-6-yl) doxorubicin (4'f(B), 0.3 g), prepared as described in Example 9, was converted into the title compound 4f(B)(MM) by treatment with 1-methoxy-2,2'-oxydiacetaldehyde and reduction with sodiumcyanoborohydride following the same procedure described in Example 7. $R_f$=0.50 (system B) FAB-MS: 787

Example 13

Preparation of N-oxysuccinimidyl derivative of 14-O-[2-carboxymethyloxymethyl-tetrahydropyran-6-yl]-3'-deamino-3'|2(S)-methoxy-4-morpholino) doxorubicin Mixture of isomers 2"R,6"R; 2"S,6"S; 2"S,6"R; 2"R,6"S

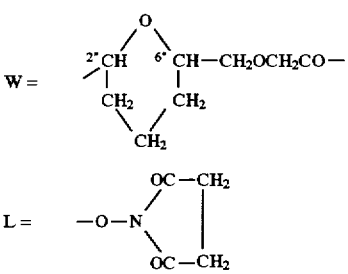

Product 4f(B)(MM), prepared in Example 12, (0.03 g, 0.037 mmole), dissolved in dimethylformamide (3 ml) and added with N-hydroxysuccinimide was transformed into the title compound 5f(B)(MM) (Example 8); $R_f$=0.55 (system H). FAB-MS: 882

Example 14

Preparation of 14-O-(6-piperazinecarbonyltetrahydropyran-2-yl)-3'-deamino-3'|2(S)-methoxy-4-morpholinyl| doxorubicin: x and y isomers (2"R,6"R ans 2"S, 6"S)

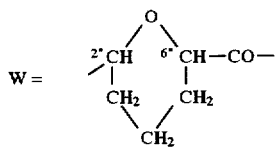

N-oxysuccinimidyl derivative of 14-O-(2-carboxytetrahydro-pyran-6-yl)-3'-deamino-3'|2(S)-methoxy-4-morpholinyl]doxo-rubicin 5f(A)(MM), 100 mg|, prepared as described in Example 8, was dissolved in anhydrous tetrahydrofurane (20 ml), cooled at 0° C. and added with a solution of 1,4-piperazine (50 mg) in anhydrous tetrahydrofurane (2 ml). The reaction mixture was stirred at Q·C for 15 minutes, then was diluted with methylene chloride (100 ml), washed with water (3×50 ml). The organic phase was separated, dryied over anhydrous sodium sulphate and the solvent was removed under reduced pressure. The crude product was chromatographed on silicic acid column using as eluting system a mixture of methylene chloride/methanol (80/20 by volume). The title compound 7f(A)(MM) (80 mg) was precipitated with ethyl ether. TLC on KIESELGEL Plate (Merck) $F_{254}$ eluting system methylene chloride/methanol (70/30 by volume) $R_f$=0.55 FD-MS: m/z 839

Example 15

Preparation of 14-O-(6-hydrazinocarbonyltetrahydropyran-2-yl)-3'-deamino-3'|2(S)-methoxy-4-morpholiny|doxorubicin x and y isomers (2"R,6"R ans 2"S,6"S)

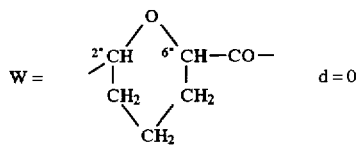 d = 0

N-oxysuccinimidyl derivative of 14-O-(2-carboxytetrahydro-pyran-6-yl)-3 '-deamnino-3'|2(S)-methoxy-4-morpholinyl]doxo-rubicin 4f(A)(MM), 100 mg), prepared as described in Example 8, was dissolved in anhydrous tetrahydrofurane (20 ml) and added with 1M solution of hydrazine hydrate in isopropanol (5 ml). The mixture was kept at 0° C. for 1 hour. After that, methylene chloride was added and the mixture was washed three times mith cold water. The organic layer was separated, dryied over anhydrous sodium sulphate, filtered and the solvent removed under vacuum. The residue was purified on silicic acid column using a mixture of methylene chloride/methanol (99/1 by volume). The title compound 6f(A)(MM) (95 mg) was precipitated with ethyl ether. TLC on KIESEL-GEL Plate (Merck) $F_{254}$ , eluting system methylene chloride/methanol (95/5 by volume) $R_f$=0.23 FD-MS: m/z 785

$^1$HNMR (200 MHz, CDCl$_3$): δ: 1.36 (d, J=6.6Hz, 3H, 5'-CH$_3$); 1.2–2.2 (m, 9H, 3"-CH$_2$, 4"-CH$_2$, 5"-CH$_2$, 2'-CH$_2$, 8ax-H); 2.3–2.7 (m, 6H, 3'-H, 8e–H, NCH$_2$CH$_2$O, NCH$_2$— CH(OCH$_3$)O); 2.9–3.4 (m, 2H, 10-CH$_2$); 3.38 (s, 3H, NCH$_2$CH(OCH$_3$)O); 3.55, 3.90 (two m, 2H, NCH$_2$CH$_2$O); 3.68 (m, 1H, 4'-H); 3.95 (m, 1H, 5'-H); 4.08 (s, 3H, 4-OCH$_3$); 4.38 (m, 1H, 6"-H); 4.49 (m, 1H, NCH$_2$CH (OCH$_3$)O); 4.6–4.9 (m, 2H, 14-C$_2$); 4.97 (m, 1H, 2"-H); 5.29 (m, 1H, 7-H); 5.54 (m, 1H, 1'-H); 7.39 (d, J=7.6Hz, 1H, 3-H); 7.59 (bd, J=6.8 Hz, 1H, CON); 7.78 (t, J=7.6 Hz, 1H, 2-H); 8.03 (d, J=7.6 Hz, 1H, 1-H); 13.29 (s, 1H, 11-OH); 13.98 (s, 1H, 6-OH).

Example 16

Preparation of anti-human melanoma conjugate 1$^1$.

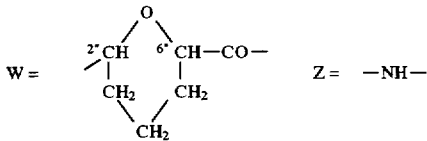

A 10$^{-2}$M solution of compound 5f(A)(MM) (Example 8), in dimethylformamide (38 mcl) was added to 1 ml of a 2 mg/ml solution of purified mouse monoclonal anti-human melanoma antibody Epl (P. Giacomini, O. Segatto, P. G. Natali, Int. J. Cancer 39, 1987, 729) in PBS pH 7.5 buffer. The reaction mixture was stirred overnight at room temperature and clarified by centrifugation. The product was isolated by gel filtration chromatography over a SEPHADEX G-25 column (PD-10, Pharmacia) eluting with PBS pH 7.5. The excluded peak was collected (2 ml) and assayed for anthracycline content spectrophotometrically at 480 nm. The protein content was assayed with a colorimetric protein analysis (BCA, Pierce). The conjugate 1$^1$ contained 0.98 mg/ml of antibody with an anthracycline:protein ratio of 8.7:1. The chemicophysical profile of the product was determined by HPLC gel filtration analysis with dual wavelenght detection (280 and 480 nm) and by SDS-PAGE. By HPLC, the molecular weight of the product was around 160 kD and the 480 nm anthracycline absorption was in correspondence with the same molecular weight. Proof of the covalent bond formation was obtained by SDS-PAGE, were both the 480 nm anthracycline absorption and the Coomassie-dye protein reaction are located at 160 kD molecular weight.

Example 17

Preparation of anti-colon carcinoma conjugate 1$^2$

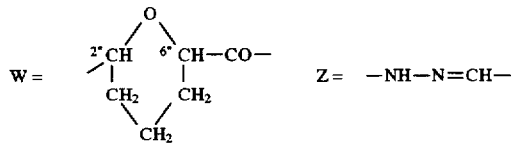

A solution of B72.3 antibody (U.S. Pat. No. 4,522,918, 1985) at 2.6 mg/ml in 0.1M phosphate buffer, pH 6, (1 ml) was treated with 0.1 ml of a 0.1M solution of NaIO$_4$ in water, at 4° C. in the dark. After 1 hour the product was purified by gel filtration chromatography over a SEPHADEX G-25 column (PD-10, Pharmacia) eluting with 0.1M phosphate buffer, pH 6. The protein-containing fraction (1.7 mg, 2 ml) was treated with 30 molar equivalents of a 10$^{-2}$M solution of compound 6f(A)(MM) (Example 15) in dimethylformamide. After 24 hours at 37° C. in the dark, the reaction mixture was centrifuged and purified by gel filtration chromatography over a SEPHADEX G-25 column (PD-10, Pharmacia) eluting with 0.1M phosphate buffer, pH 7.3. The protein-containing peak was collected (2 ml) and characterized as for Example 16. The conjugate $1^2$ contained 0.45 mg/ml of antibody with an anthracycline/protein ratio of 1.3/1 and displayed an analytical profile analogous to the conjugate obtained in Example 16.

Example 18

Preparation of anti-transferrin receptor conjugate $1^3$

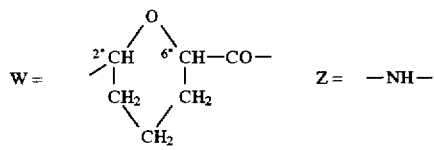

A $10E^{-2}M$ solution of compound 5f(A)(MM) (described in Example 8) in N,N-dimethylformamide (37 mcl) was added to 1 ml of a 2 mg/ml solution of a purified mouse monoclonal anti-human transferrin receptor antibody OKT9 (Sutherland, R., Delia, D., Schneider, C., Newman, R., Kemshead, J., Greaves, M., Proc. Nat. Acad. Sci. USA, 78 (1981), 4515; ATCC CRL 8021) in 0.1M NaH2PO4, 0.1M NaCl, pH 8 buffer. The reaction mixture was stirred overnight at room temperature in the dark and clarified by centrifugation. The title conjugate $1^3$ was isolated by gel filtration chromatography over a SEPHADEX G-25 column (PD-10, Pharmacia, Cat. No. 17-0851-01) eluting with PBS pH 7.3 (Gibco, 10X, Cat. N. 042-04200M). The excluded peak was collected and analyzed for anthracycline content (spectrophotometrically at 480 nm) and for protein content (BCA Protein Assay Reagent, Pierce, Cat. 23225). The conjugate contained 1.94 mg/ml of antibody and 80.9 mcg/ml of anthracycline, with an anthracycline:protein molar ratio of 9.5. The analytical profile of the product was evaluated as in Example 16, with similar results.

Example 19

Preparation of anti-colon carcinoma conjugate $1^4$

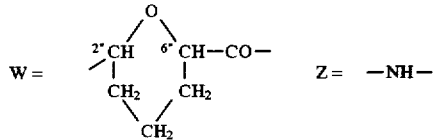

A conjugate of formula $1^4$, containing 0.74 mg/ml of protein and 27.5 mcg/ml of anthacycline, with an anthracycline/protein ratio of 9.1, was obtained with operating as in Example 18 and using in place of OKT9, a solution of B72.3 antibody (2.3 mg/ml) [Schlom, J. et al., U.S. Pat. No. 4,522,918 (1985)] and 43 mcl of the solution of 5f(A)(MM).

Example 20

Preparation of anti-epidermal growth factor conjugate $1^5$

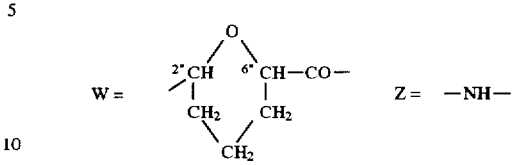

Conjugate $1^5$, containing 0.49 mg/ml of protein and 14.3 mcg/ml of anthracycline, with an anthracycline/protein ratio of 6.9, was obtained with operating as in Example 18 and using in place of OKT9, a solution of an anti-epidermal growth factor receptor antibody (1.15 mg/ml) (BioMacor Cat. No. 6080, Clone 29.2) and 13 mcl of the solution of compound 5f(A)(MM).

Example 21

Preparation of anti-transferrin receptor conjugate $1^6$

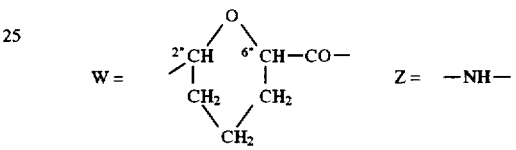

The title compound $1^6$, containing 0.34 mg/ml of protein and 5.3 mcg/ml of anthracycline, with an anthracycline/protein ratio of 3.9, was obtained with operating as in Example 18 and using in place of OKT9 a solution of the anti-transferrin receptor antibody B3/25 (0.5 mg/ml) (Boehringer Cat. No. 1118 048) and 9.4 mcl of the solution of 5f(A)(MM).

Example 22

Preparation of FGF conjugate $1^7$

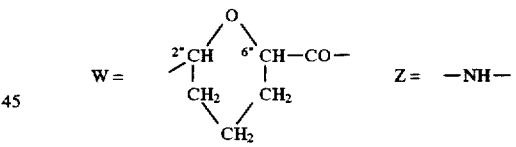

Compound $1^7$ containing 0.77 mg/ml of protein and 117 mcg/ml of anthracycline, with an anthracycline/protein ratio of 3.4, was prepared with operating as in Example 18 and using in place of OKT9, a solution of human recombinant FGF (1.35 mg/ml)(Barr et al, J. Biol. Chem. 263 (1988), 16471) and 48 mcl of the solution of 5f(A)(MM).

Example 23

Preparation of anti-transferrin receptor conjugate $1^8$

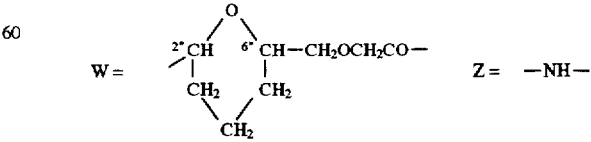

Conjugate $1^8$, containing 0.46 mg/ml of protein and 13 mcg/ml of anthracycline, with an anthracycline/protein ratio of 4.90 was obtained with operating as in Example 18 and using 37 mcl of a $10E^{-2}M$ solution of 5f(B)(MO) (Example 11).

Example 24

Preparation of anti-colon carcinoma conjugate $1^9$

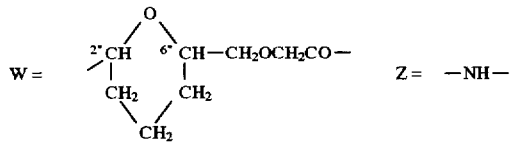

Conjugate of formula $1^9$ containing 0.46 mg/ml of protein and 8.38 mcg/ml of anthracycline, with an anthracycline:protein ratio of 4.5 was obtained with operating as in Example 18 and using in place of OKT9, the anti-colon carcinoma antibody B72.3 and 43 mcl of a $10E^{-2}M$ solution of 5f(B)(MO) (Example 11).

Example 25

Preparation of anti-transferrin receptor conjugate $1^{10}$

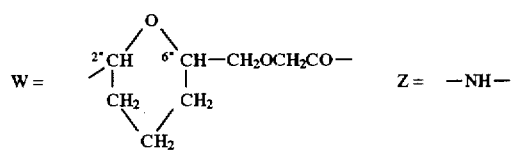

Compound $1^{10}$ containing 0.67 mg/ml of protein and 20.3 mcg/ml of anthacycline, with an anthracycline/protein ratio of 7.6 was obtained with operating as in Example 18 and using 37 mcl of a $10E^{-2}M$ solution of 5f(B) (MM) (Example 13).

Example 26

Preparation of anti-colon carcinoma conjugate $1^{11}$

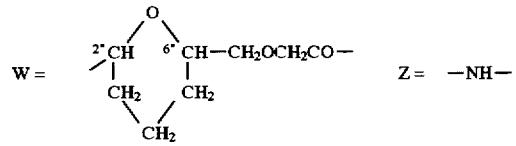

Operating as in Example 18 and using in place of OKT9, the anti-colon carcinoma antibody B72.3 and 43 mcl of a $10E^{-2}M$ solution of compound 5f(B)(MO), was prepared the title compound $1^{11}$ containing 0.55 mg/ml of protein and 7.4 mcg/ml of anthracycline, with an anthracycline/protein ratio of 3.2.

Example 27

Preparation of conjugate of Poly(Glu.Na.Ala.Tyr) (1:1:1) $1^{12}$

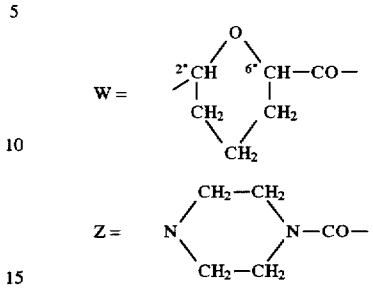

Poly(Glu.Na.Ala.Tyr) (1:1:1) $M_w$ 25000–40000 (Sigma), (0.2 g) was dissolved in water (5 ml) under stirring at room temperature. The corresponding free acid was precipitated from the aqueous solution at pH 3 by means of 0.1N HCl. Poly(Glu—OH.Ala.Tyr) (0.17 g), recovered and dryied under vacuum, was dissolved in dry dimethylformamide (10 ml) and added with 14-O-($^6$-piperazinecarbonyltetrahydropyran-2-yl)-3'-deamino-3'|2 (S)-methoxy-4-morpholinyl|doxorubicin (|7f(A)(MM), 0.035 g] (described in Example 14) and N-ethoxy-carbonyl-2-ethoxy-1,2-dihydroquinoline (EEDQ) (0.08 g). Another aliquot of EEDQ (0.08 g) was added after three hours. The reaction mixture was stirred overnight at room temperature, than was poured in ethyl ether (300 ml). The precipitated was suspended in water (10 ml) and treated with 0.1N NaOH (14 ml); the solution was brought to pH 8.5 with 0.1N HCl and passed on a column of SIPHADEX G10. The aqueous solution was liophilized to give 0.16 g of the title compound $1^{12}$. Content of anthracycline (w/w %) calculated as 3'-deamino-3'|2(S)-methoxy-4-morpholinyl|doxorubicin hydrochloride: 10%

Example 28

Preparation of conjugate of Poly-L-Glutamic acid $1^{13}$

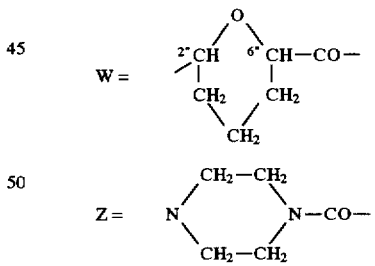

Poly-L-Glutamic acid, $M_w$ 2000–15000 (Sigma) (0.1 g) and 14-O-(6-piperazinecarbonyltetrahydropyran-2-yl)-3'-deamino-3'[2(S)-methoxy-4-morpholinyl]doxorubicin [7f (A)(MM), 0.03 g], (described in Example 14), were dissolved in anhydrous dimethylformamide (2 ml) and stirred for three hours. After that, N-ethoxy-carbonyl-2-ethoxy-1, 2-dihydro-quinoline (EEDQ) (0.03 g) was added. The mixture was kept under stirring overnight, then was poured into a mixture of ethyl ether and petroleum ether. The precipitate was collected on a sintered glass filter, washed with ethyl ether and dissolved with a 2.5% aqueous solution of sodium hydrogen carbonate (8 ml). The solution was passed through a reverse phase column RP-8, 40–63 μm (Merck) (30×1.8 cm) and eluted with a mixture of water and acetonitrile. The eluate containing the conjugate was liophilized then collected on a sintered glass filter, washed with methanol and ethyl ether to give the title compound $1^{13}$ (65 mg). By spectroscopic evaluation, the conjugate contains 16%% (w/w %) of 3'-deamino-3'|2(S)-methoxy-4-morpholinyl| doxorubicin hydrochloride.

Example 29

Preparation of conjugate of Poly-L-Glutamic acid $1^{14}$

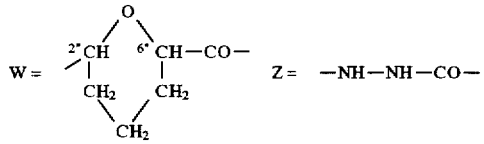

Following the same procedure described in Example 28, Poly-L-Glutamic acid, $M_w$ 2000–15000 (Sigma) (0.1 g) and 14-O-(6-hydrazinocarbonyltetrahydropyran-2-yl)-3'-deamino-3'|2(S)-methoxy-4-morpholiny|doxorubicin |6f (A)(MM), 0.05 g|, (described in Example 15) were reacted in dimethylformamide in presence of EEDQ. After work up and purification on RP-8, 40–63 µm (Merck) column, 50 mg of the title compound $1^{14}$ was collected. By spectroscopic evaluation, the conjugate contains 12% (w/w %) of 3'-deamino-3'|2(S)-methoxy-4-morpholinyl|doxorubicin hydrochloride.

Example 30

Evaluation of the cell binding activity of the anti-transferrin receptor conjugate $1^3$ on a human melanoma cell line Ref.: Matsui, M. et al., J. Immunology, 141 (1988) 1410 Bumol, T. F. et al., Antibody-Mediated Delivery Systems, Rodwell, J. D. Ed., (1988) 55 Harper, J. R. et al., Anal. Biochem., 113 (1980) 51

M10 human melanoma cells (ATCC CRL 8021) in RPMI 1640 medium (PBI 12/167B), 10% FCS (Flow Laboratories 29101-54), 1% glutamine were plated in 96 well microtiter plates (Costar 3596) (10000 cells/well). After 16 h at 37° C., cells were washed with PBS, 3% FCS and incubated with different concentrations of the conjugate $1^3$ (Example 18), or of the OKT9 antibody, in PBS, 3% FCS 100 mcl, 5–1000 ng/ml for 1 h at 37° C. After three washings with PBS, 3% FCS, 100 mcl of a 1:1500 diluition of horseradish peroxidase conjugated goat anti-mouse IgG (BioRad 172-1011) were added to each well.

Plates were then incubated for one hour at 37° C. and washed three times with PBS, 3% FCS. Then, 100 mcl of a freshly prepared substrate solution of o-phenylendiamine dihydrochloride (Sigma P6912) (0.5 mg/ml) and H2O2 (0.015%), in H2O were added to each well. After a 30'incubation at 37° C. the reaction was stopped by the addition of 25 mcl of 4.5N H2SO4 to each well, and absorbance was read at 495 nm with a BioRad EIA Reader Model 2550. The conjugate displayed a good retention of cell binding activity in comparison with the parent antibody as shown in FIG. 1.

Example 31

Evaluation of the selective cytotoxicity of the anti-transferrin receptor conjugate $1^3$ Ref.: Dillman, R. O. et al., Cancer Res., 48 (1988) 6097 Ahmad, A. et al., Anticancer Res., 10 (1990) 837

Figure 2:
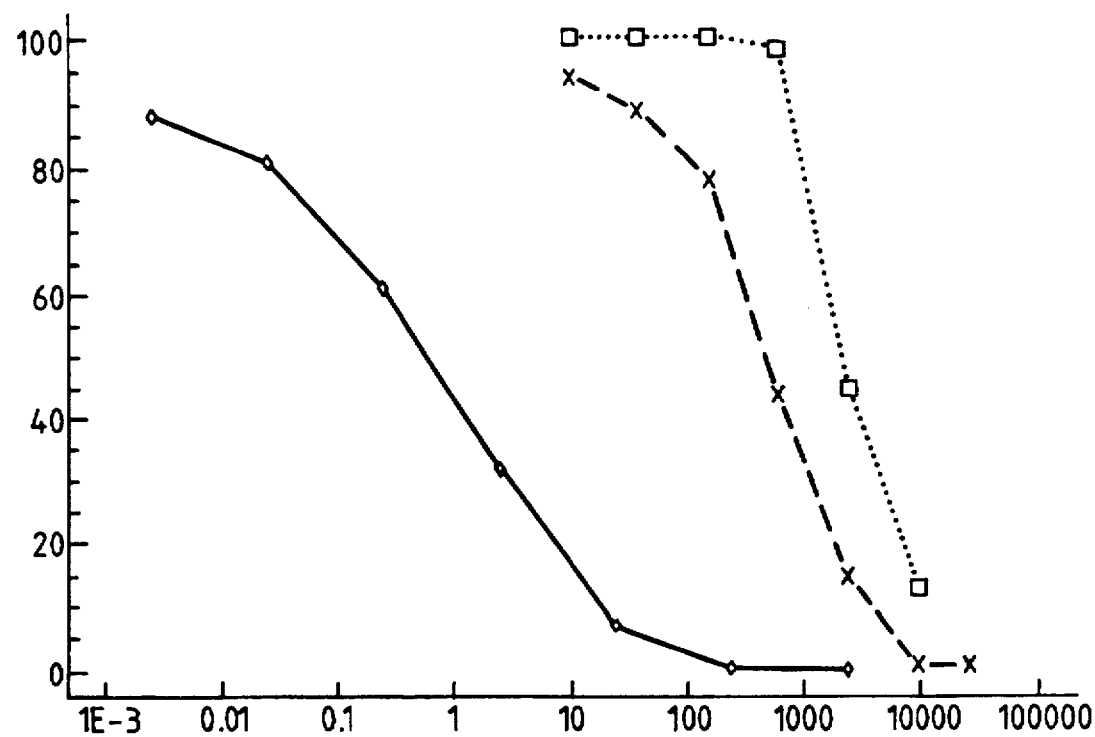
FIG. 2 is a graph showing the results of an evaluation, reported in Example 31 which follows, of the selective cytotoxicity of an anti-transferrin receptor immunoconjugate $1^3$ of the invention (line X—X—X), of an irrelevant control conjugate (line ▫—▫—▫) and of the parent free anthracycline drug (line ◊—◊—◊). In the graph (3H) Thymidine incorporation, as a percentage of control (y axis), is plotted against anthracycline concentration in nM (x axis).

M10 human melanoma cells (ATCC CRL 8021) were plated in 96 well plates (Costar 3596) in 200 mcl RPMI 1640 (PBI 12/167B) containing 10% FCS (Flow Laboratories 29101-54), 1% glutamine, (10000 cells/well) at 37° C. After 18 h, the culture medium was removed and 100 mcl of fresh medium were added. Fifty microliters of different concentrations of the conjugate $1^3$ and of the relative controls in PBS, 3% FCS, were added to triplicate wells. Plates were incubated for 24h at 37° C., then 0.8 microCurie/well of (3H)thymidine (NEN DuPont NET 355) were added in 20 mcl of medium and incubation was continued at 37° C. for 7 h. Cells were harvested with a Dynatech MultiMash 2000 cell harvester onto filter paper (Whatman 1827842), filters were air dried, placed in vials with scintillation fluid (Kontron Analytical Supertron 56920-04010) and counted in a scintillation counter (Kontron Instrument Betamatic). All the conjugates were substantially less cytotoxic than the parent drug, but the specific anti-transferrin receptor conjugate displayed an effect fivefold superior to an irrelevant control conjugate, as the comparison between the IC50 of the two compounds shows. Results from a typical experiment are shown in FIG. 2.

Example 32

Inhibition of cytotoxicity of the anti-transferrin receptor immunoconjugate $1^3$ by unconjugated antibody Ref.: Chaundhary, V. K. et al., Nature 339 (1989) 394 Batra, J. K. et al.: Mol. and Cell. Biol. 11 (1991) 2200 Siegal, C. B. et al., J. Biol. Chem. 265 (1990) 16318

Figure 3:
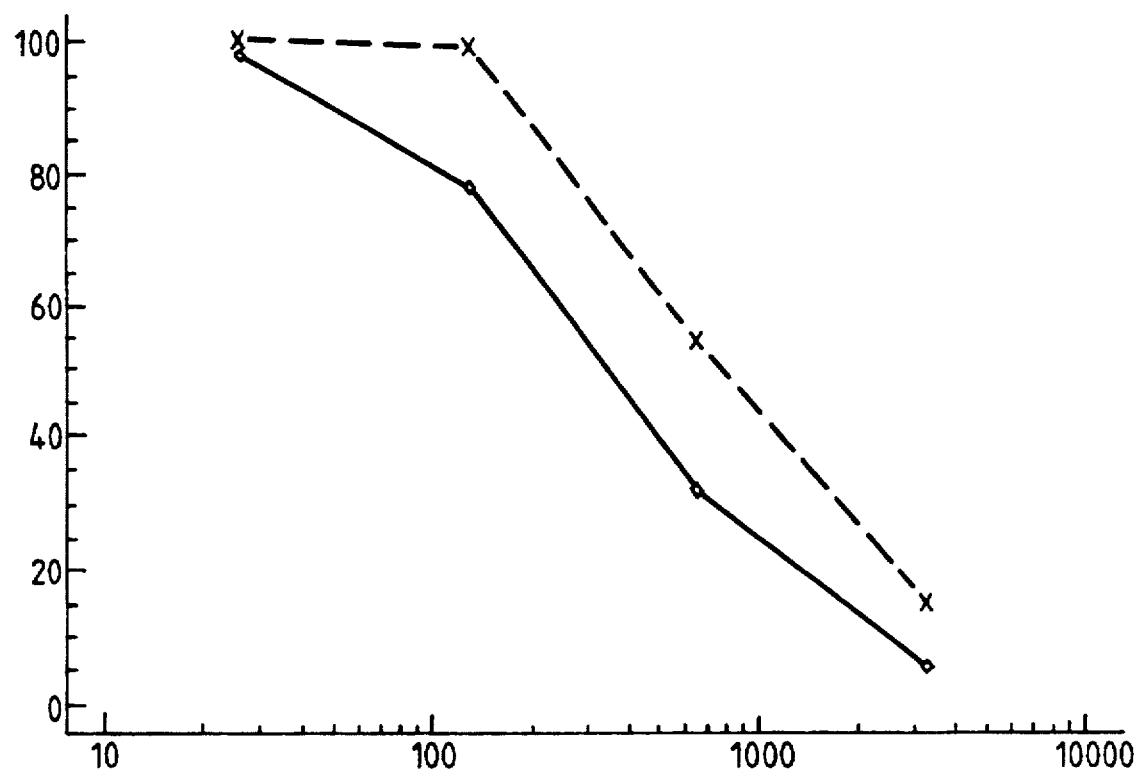
FIG. 3 is a graph showing the results of an evaluation, reported in Example 32 which follows, of the inhibition of cytotoxicity of the antitransferrin receptor conjugate $1^3$ by unconjugated antibody. Line X—X—X—= immunoconjugate. $1^3$+OKT9 antibody and line ◊—◊—◊=immunoconjugate $1^3$. The (3H) Thymidine incorporation, as a percentage of control (y axis), is plotted against anthracycline concentration in nM.

M10 human melanoma cells (ATCC CRL 8021) were plated in 96 well plates (Costar 3596) in 200 mcl RPMI 1640 (PBI 12/167B) containing 10% FCS (Flow Laboratories 29101-54), 1% glutamine (10000 cells/well) at 37° C. After 18 h, the culture medium was removed and 50 mcl of fresh medium were added. Then, 50 mcl of a solution of OKT 9 antibody in complete culture medium were added to triplicate wells (final concentration in wells from 7000 to 56 mcg/ml). Control wells were treated with 50 mcl of complete culture medium. Plates were incubated for 1 h at 4° C., then 50 mcl of different concentrations of the conjugate $1^3$, in complete culture medium, were added (final concentration of antibody in wells from 70 to 0.56 mcg/ml, corresponding to a 1:100 molar excess of free antibody added in the previous step). After 24 h at 37° C., 0.8 microCurie/well of (3H)thimidine (NEN DuPont NET 355) in 20 mcl of medium were added, and incubation was continued at 37° C. for 7 h. Cells were harvested and radioactivity incorporation was evaluated as in Example 31. As shown in FIG. 3, free antibody addition inhibits the cytotoxicity of the immunoconjugate over a range of doses of anthracycline content, thus confirming the receptor mediated effect of the compounds herein described. Results from a typical experiment are shown in FIG. 3.

Example 33

Dose-response inhibition of cytotoxicity of the anti-transferrin receptor immunoconjugate $1^3$ by unconjugated antibody Ref.: Chaundhary, V. K. et al., Nature 339 (1989) 394 Batra, J. K. et al.: Mol. and Cell. Biol. 11 (1991) 2200 Siegal, C. B. et al., J. Biol. Chem. 265 (1990) 16318

Figure 4:
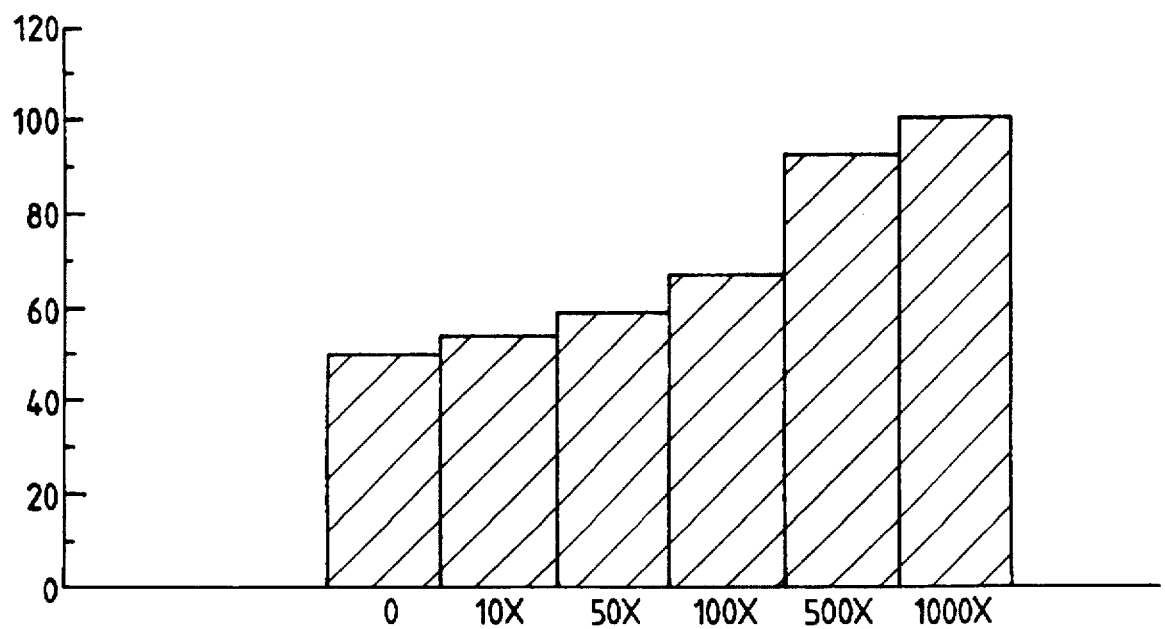
FIG. 4 depicts the dose-response inhibition of cytotoxicity of the anti-transferrin receptor immunoconjugate $1^3$ by different excess amounts of unconjugated antibody OKT9, as described in Example 33 which follows. In the graph, (3H) Thymidine incorporation as a percentage of control (y axis) is plotted against free antibody excess (x axis).

M10 cells were plated and incubated for 18 h as described in Example 32. After that, the culture medium was removed and 50 mcl of fresh medium were added. Then, 50 mcl of a solution of OKT9 antibody in complete culture medium were added to triplicate wells (final concentration in wells from 2120 to 21.2 mcg/ml). Control wells were treated with 50 mcl of complete culture medium. Plates were incubated for 1 h at 4° C. Then, 50 mcl of the conjugate $1^3$ in complete culture medium, were added (final concentration of antibody in wells 2.12 mcg/ml). Cells were incubated, harvested and radioactivity incorporation evaluated as in Example 31. As FIG. 4 shows, a dose-response related inhibition of conjugate cytotoxicity is effected by the pre-treatement of cells with different excesses of unconjugated antibody, confirming the receptor-mediated cytotoxicity of the compounds.

Example 34

Evaluation of the selective cytotoxicity of the FGF conjugate $1^7$

Figure 5:
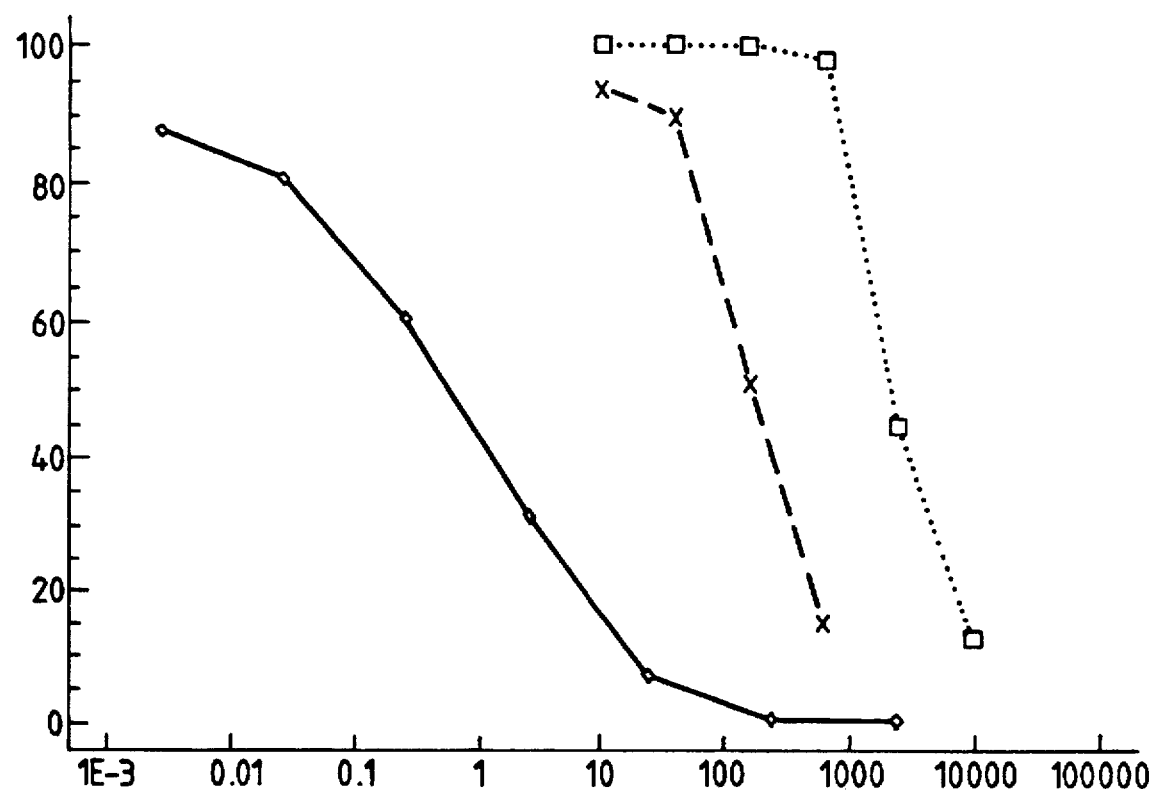
FIG. 5 shows the results of an evaluation, reported in Example 34 which follows, of the selective cytotoxicity of the FGF conjugate $1^7$ (line X—X—), of an irrelevant immunoconjugate control $1^4$ (linen ▫—▫—▫) and of free anthracycline (line ◊—◊—◊). In the graph (3H) Thymidine incorporation, as a percentage of control (y axis), is plotted against anthracycline concentration in nM (x axis).

Operating as in Example 31 and utilizing the conjugate of formula $1^7$, the selective cytotoxicity of the FGF conjugate was demonstrated (FIG. 5).

Example 35

Utilizing the protocol described in Example 31 and different combinations of anthracyclines, linkers, and targeting carriers, different conjugates were prepared, and their cytotoxicity was tested on different cell lines, utilizing non binding conjugates as controls. As Table 1 indicates, specific conjugates are consistently more efficient in inhibiting the growth of tumor cells in comparison with control, non binding, conjugates. The ratio between the IC50 may be taken as an index of the selectivity of the compounds. Thus, from 7% to 38% of a specific conjugate is as cytotoxic as a 100% dose of a control conjugate. The selectivities observed were confirmed from experiments performed with different anthracyclines, linkers, target cells, and for various times of incubation.

TABLE 1

SELECTIVE CYTOTOXICITY OF ANTHRACYCLINE CONJUGATES

| Specific Conjugate | Control Conjugate | Target Cells | Incubation Time (h) | IC50 × 10E7 Spec./Contr | IC50 Ratio |
|---|---|---|---|---|---|
| $1^3$ | $1^4$ | M10 | 24 | 5.0/21.0 | 0.23 |
| " | " | " | 48 | 1.2/6.8 | 0.17 |
| " | " | " | 72 | 1.7/5.6 | 0.30 |
| " | " | M14 | 48 | 3.9/16.0 | 0.24 |
| " | " | " | 72 | 5.0/17.0 | 0.29 |
| " | " | OVCAR3 | 72 | 4.1/18.0 | 0.23 |
| " | " | A431 | 24 | 9.1/40.0 | 0.23 |
| $1^5$ | " | " | 24 | 18.0/40.0 | 0.45 |
| $1^7$ | " | M10 | 24 | 1.5/21.0 | 0.07 |
| $1^6$ | " | " | 48 | 5.1/10.0 | 0.51 |
| $1^5$ | " | M14 | 48 | 11.0/20.0 | 0.55 |
| $1^8$ | $1^9$ | M10 | 24 | 1.0/9.0 | 0.11 |
| " | " | " | 72 | 0.4/2.3 | 0.17 |
| " | " | M14 | 24 | 1.2/11.0 | 0.10 |
| " | " | " | 72 | 1.6/12.0 | 0.13 |
| $1^{10}$ | $1^{11}$ | M10 | 24 | 2.2/9.0 | 0.24 |
| " | " | " | 72 | 3.0/8.0 | 0.38 |
| " | " | M14 | 24 | 5.1/>10.0 | n.d. |
| " | " | " | 72 | 6.0/>10.0 | n.d. |

Target cells references:
M10: human melanoma, ATCC CRL 8021
M14: human melanoma, Natali, P. G. et al., J. Immunol. Meth. 62 (1983), 337
OVCAR-3: human ovaric carcinoma, ATCC HTB 161
A431: human epidermoid carinoma, ATCC CRL 1555

Example 36

Evaluation of compound $1^{14}$

Compound $1^{14}$ was evaluated "in vivo" against P388 murine Leukemias resistant to Doxorubicin in comparison with 3'-deamino-3'|2(S)-methoxy-4-morpholino|doxorubicin (DMM) and doxorubicin. Data are reported in Table 2. The conjugate showed similar antitumor activity, but at higher doses, of the free drug.

TABLE 2

Antitumor activity against P388/DX (Johnson) Leukemia.
P388/DX[1]

| compound | dose[2] (mg/kg) | T/C[3] % | TOX |
|---|---|---|---|
| $1^{14}$ | 5.2[4] | 200 | 0/10 |
| Doxorubicin | 16.9 | 100 | 0/10 |
| DMM[5] | 0.09 | 192 | 0/39 |

[1]$10^5$ cells/mouse (P388/DX, Johnson) transplanted i.v. in CDF1 mice. Treatment on day 1 after inoculation of tumor.
[2]Optimal Dose
[3]Median survival time % over untreated controls
[4]Dose of active drug: 3'-deamino-3'|2(S)-methoxy-4-morpholino| doxorubicin (DMM)
[5]3'-deamino-3'|2(S)-methoxy-4-morpholino|doxorubicin

We claim:

1. A conjugate of the formula 1:

$$(A-O-W-Z)_a-T \qquad (1)$$

wherein the moiety A—O— is the residue of an anthracycline bearing a primary hydroxyl group such that the group —O— derives from the hydroxyl group in the 14 position of the anthracycline moiety, and the 3,'-position of said anthracycline is substituted with a morpholino moiety;

a is an integer of from 1 to 30;

W is a residue of formula 2:

$$\qquad (2)$$

wherein B is a —CH$_2$OCH$_2$— group and m is 0 or 1;

Z is a spacer group selected from the group consisting of —NH—, —NH—N=CH—, —NH—NH—CO—, and a piperazinylcarbonyl moiety; and T is the residue of a carrier moiety of formula T—NH$_2$, T-(CHO)$_a$, or T -|COOH|$_a$ wherein a is as defined above, the carrier moiety being selected from the group consisting of a polyclonal antibody, a fragment of a polyclonal antibody which comprises an antigen binding site and is capable of binding to a tumor associated antigen, a monoclonal antibody, and a fragment of a polyclonal antibody which comprises an antigen binding site and is capable of binding to an antigen which is preferentially or selectively expressed on a tumor cell population.

2. A conjugate according to claim 1, wherein the anthracycline bearing a one primary hydroxyl group has the formula 3:

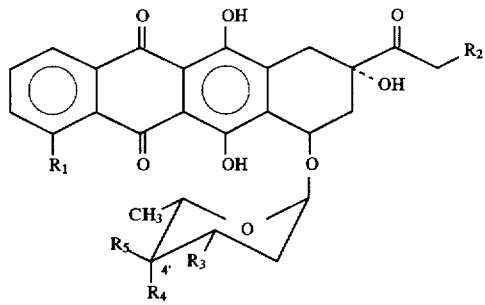

in which:

$R_1$ is a hydrogen atom, a hydroxy or a methoxy group;

$R_2$, $R_4$ and $R_5$ take the values set out in the table below:

| $R_2$ | $R_4$ | $R_5$ |
|---|---|---|
| OH | H | OH |
| OH | OH | H |
| OH | I | H |
| OH | H | H | and $R_3$ represents a nitrogen atom enclosed in a morpholino ring.

3. A conjugate according to claim 2, wherein the moiety A—O— represents:

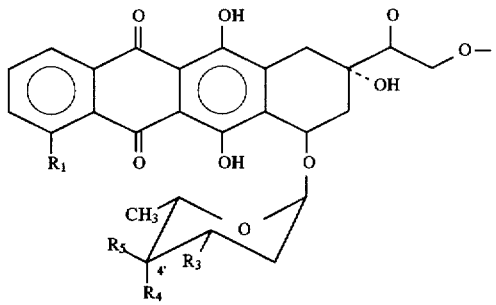

in which $R_1$ and $R_3$ are as defined in claim 2 and one of $R_4$ and $R_5$ is a hydrogen atom and the other of $R_4$ and $R_5$ is a hydroxy group or $R_4$ is a hydrogen or iodine atom and $R_5$ is a hydrogen atom.

4. A conjugate according to claim 1, wherein the carrier is selected from an anti-T-cell antibody, an anti-CD5 antibody, an anti-transferrin receptor antibody, and anti-melanoma antibody, an anti-carcinoma marker antibody, an anti-ovarian carcinoma antibody, an anti-breast carcinoma antibody and an anti-bladder carcinoma antibody.

5. A method for the treatment of tumours which method comprises administering to a patient in need of such treatment a pharmaceutically effective amount of a conjugate of formula 1 as defined in claim 1.

6. A pharmaceutical composition suitable for use as an anti-tumor agent, said composition comprising a pharmaceutically acceptable carrier or diluent and, as active ingredient, a therapeutically effective amount of a conjugate as claimed in claim 1.

* * * * *